US008655453B2

(12) United States Patent
Werder et al.

(10) Patent No.: US 8,655,453 B2
(45) Date of Patent: Feb. 18, 2014

(54) CONNECTING ELECTRICAL SOURCES TO ELECTRODE NODES IN A MEDICAL DEVICE

(75) Inventors: Jonathan C. Werder, Corcoran, MN (US); Todd D. Heathershaw, Chandler, AZ (US)

(73) Assignee: Medtronic, Inc., Minneapolis, MN (US)

( * ) Notice: Subject to any disclaimer, the term of this patent is extended or adjusted under 35 U.S.C. 154(b) by 796 days.

(21) Appl. No.: 12/541,611

(22) Filed: Aug. 14, 2009

(65) Prior Publication Data

US 2010/0042187 A1 Feb. 18, 2010

Related U.S. Application Data

(60) Provisional application No. 61/088,965, filed on Aug. 14, 2008.

(51) Int. Cl.
*A61N 1/04* (2006.01)
(52) U.S. Cl.
USPC .......................................................... 607/74
(58) Field of Classification Search
USPC .......................................................... 607/74
See application file for complete search history.

(56) References Cited

U.S. PATENT DOCUMENTS

| 5,344,429 | A | * | 9/1994 | Smits .................................. 607/5 |
| 5,470,341 | A | * | 11/1995 | Kuehn et al. ....................... 607/5 |
| 5,757,167 | A | * | 5/1998 | Arora et al. .................... 323/224 |
| 6,038,477 | A | | 3/2000 | Kayyali |
| 6,181,969 | B1 | | 1/2001 | Gord |
| 6,473,653 | B1 | | 10/2002 | Schallhorn et al. |
| 6,516,227 | B1 | | 2/2003 | Meadows et al. |
| 6,895,280 | B2 | | 5/2005 | Meadows et al. |
| 7,024,246 | B2 | | 4/2006 | Acosta et al. |
| 7,127,298 | B1 | | 10/2006 | He et al. |
| 7,180,760 | B2 | | 2/2007 | Varrichio et al. |
| 2007/0100399 | A1 | | 5/2007 | Parramon et al. |
| 2007/0293914 | A1 | | 12/2007 | Woods et al. |
| 2010/0286749 | A1 | * | 11/2010 | Parramon et al. ............... 607/66 |

OTHER PUBLICATIONS

Reply to Written Opinion for corresponding patent application No. PCT/US2009/053865, filed Feb. 8, 2010, 13 pages.
Notification of Transmittal of the International Search Report and the Written Opinion of the International Searching Authority for corresponding patent application No. PCT/US2009/053865, mailed Oct. 29, 2009, 11 pages.
Notification of Transmittal of the International Preliminary Report on Patentability for corresponding patent application No. PCT/US2009/053865, mailed Jul. 16, 2010, 12 pages.

* cited by examiner

*Primary Examiner* — George Manuel
(74) *Attorney, Agent, or Firm* — Shumaker & Sieffert, P.A.

(57) ABSTRACT

This disclosure describes electrical stimulators that include some electrical sources (e.g., current sources, voltage sources) that are directly connected to a plurality of electrode nodes, and other electrical sources that may be selectively connected to selected ones of the plurality of electrode nodes via a switching unit, such as a multiplexer. One example stimulator comprises a processor, a plurality of electrode nodes, and a stimulation generator that is coupled to the processor and to the plurality of electrode nodes. The stimulation generator comprises a plurality of negative electrical sources, a switching unit, and at least one positive electrical source. The negative electrical sources are each directly connected to a different one of the plurality of electrode nodes. The switching unit is connected to each of the plurality of electrode nodes. The at least one positive electrical source is connected to the switching unit. The switching unit is configured to connect the at least one positive electrical source to a selected one or more of the plurality of electrode nodes.

29 Claims, 13 Drawing Sheets

CONNECTING ELECTRICAL SOURCES TO ELECTRODE NODES IN A MEDICAL DEVICE

TECHNICAL FIELD

This application claims the benefit of U.S. Provisional Application No. 61/088,965, filed Aug. 14, 2008, the entire content of which is incorporated herein by reference.

BACKGROUND

This disclosure relates to medical devices and, more particularly, stimulators that may deliver electrical stimulation to one or more electrodes.

Electrical stimulators may be used to deliver electrical stimulation therapy to patients to treat a variety of symptoms or conditions such as chronic pain, tremor, Parkinson's disease, epilepsy, urinary or fecal incontinence, sexual dysfunction, obesity, or gastro paresis, and may also be used to deliver electrical stimulation to the brain, such as in deep-brain stimulation. An electrical stimulator may deliver electrical stimulation therapy via leads that include electrodes located proximate to the spinal cord, pelvic nerves, stomach, peripheral nerves, or within the brain of a patient. In many cases, the stimulator and/or the electrodes are implanted.

A clinician selects values for a number of programmable parameters in order to define the electrical stimulation therapy to be delivered to a patient. For example, the clinician may selects an amplitude, which may be a current or voltage amplitude, and, when electrical stimulation is delivered in the form of pulses, a pulse width for a stimulation waveform to be delivered to the patient, as well as a rate at which the pulses are to be delivered to the patient. The clinician may also select particular electrodes within an electrode set to be used as an electrode combination to deliver the electrical stimulation, as well as the polarities of the selected electrodes. A set of parameter values may be referred to as a program in the sense that they drive the electrical stimulation therapy to be delivered to the patient.

In some cases, electrical stimulation is delivered via electrodes carried by one, two or more implantable leads, each of which may include multiple electrodes. Electrical stimulation may be delivered via various combinations of electrodes, including electrodes on a single lead, or electrodes on different leads. For example, one program may specify a combination of electrodes located relatively proximally on one or more leads while another program may specify a combination of electrodes located more distally on the one or more leads. In addition, some programs may include greater or lesser numbers of electrodes, greater or lesser distances between electrodes, or varied positions of cathodes and anodes. In this manner, electrical stimulation can be shaped and targeted relative to nerves, muscle or other tissue or anatomical structures to enhance therapeutic efficacy.

In some cases, an electrical stimulator may include multiple electrical sources. For example, the electrical stimulator may include multiple current sources that may each deliver current having a positive polarity (positive current sources), as well as multiple current sources that may each deliver current having a negative polarity (negative current sources). Each electrode coupled to the stimulator may be directly connected to one positive current source and one negative current source. In such fashion, the electrode may be programmed as either a cathode (when its connected negative current source is activated) or as an anode (when its connected positive current source is activated).

Some electrical stimulators have included fewer electrical sources than the number of available electrodes. Such electrical stimulators have included a multiplexer or other switching unit to connect the electrical sources to a greater number of electrodes. In such electrical stimulators, the electrical sources are not directly coupled to any electrode. In other words, in such electrical stimulators, the switching unit is always used to couple a selected electrode to an electrical source.

SUMMARY

This disclosure describes electrical stimulators that include some electrical sources (e.g., current sources, voltage sources) that are directly connected to a plurality of electrode nodes, and other electrical sources that may be selectively connected to selected ones of the plurality of electrode nodes via a switching unit, such as a multiplexer. In some examples, negative electrical sources are directly connected to the electrode nodes, while positive electrical sources are selectively connected to the electrode nodes via the switching unit. This disclosure also describes related methods, such as methods for making and using such a stimulator. An electrode node is a circuit node within a housing of the stimulator that is, for example, directly connected to a corresponding electrode on the housing, or directly connectable to a corresponding electrode on a lead when the lead is connected to the stimulator.

For at least some therapies, such as spinal cord stimulation or deep brain stimulation, stimulation at the cathode may provide a majority of the therapeutic effect, and also may be more likely to result in a side effect or negative effect. Thus, the locations and numbers of cathodes may, in some cases, be more relevant than the locations and numbers of anodes for such therapies. Embodiments that include negative electrical sources directly coupled to respective electrode nodes, rather than coupling a smaller number of electrical sources to a greater number of electrode nodes with a switching unit, may advantageously allow greater control of the location and numbers of cathodes for such therapies. Furthermore, embodiments in which multiple electrode nodes may share and be multiplexed with at least one positive electrical source, rather than each being connected to a separate positive electrical source, may reducing the number of positive electrical sources within a stimulator. This reduction in electrical sources may thereby help reduce the number of electrical components in and battery consumption of the stimulator.

In one embodiment, an implantable stimulator comprises a plurality of electrode nodes, a processor, and a stimulation generator that is coupled to the processor and the plurality of electrode nodes. The stimulation generator comprises a plurality of negative electrical sources, a switching unit, and at least one positive electrical source. The negative electrical sources are each directly connected to a different one of a plurality of electrode nodes. The switching unit is connected to each of the plurality of electrode nodes. The at least one positive electrical source is connected to the switching unit. The switching unit is configured to connect the at least one positive electrical source to a selected one or more of the plurality of electrode nodes.

In one embodiment, a stimulation generator comprises a plurality of negative electrical sources, a switching unit, and at least one positive electrical source. The negative electrical sources are each directly connected to a different one of a plurality of electrode nodes. The switching unit is connected to each of the plurality of electrode nodes. The at least one positive electrical source is connected to the switching unit.

The switching unit is configured to connect the at least one positive electrical source to a selected one or more of the plurality of electrode nodes.

In one embodiment, a method comprises directly connecting each of a plurality of negative electrical sources in a stimulation generator to a different one of a plurality of electrode nodes, connecting a switching unit in the stimulation generator to each of the plurality of electrode nodes, and connecting at least one positive electrical source in the stimulation generator to the switching unit.

In one embodiment, a method comprises using an electrode node combination for an implantable stimulator that includes a first set of one or more electrode nodes that are each connected to an anode, wherein the electrode node combination further includes a second set of one or more electrode nodes that are each connected to a cathode, and configuring a switching unit in a stimulation generator to connect at least one positive electrical source in the stimulation generator to the first set of one or more electrode nodes. The method further includes activating the at least one positive electrical source, and activating at least one negative electrical source in the stimulation generator, wherein the at least one negative electrical source is directly connected to the second set of one or more electrode nodes.

The details of one or more embodiments of the invention are set forth in the accompanying drawings and the description below. Other features, objects, and advantages will be apparent from the description and drawings, and from the claims.

DETAILED DESCRIPTION

Figure 1:
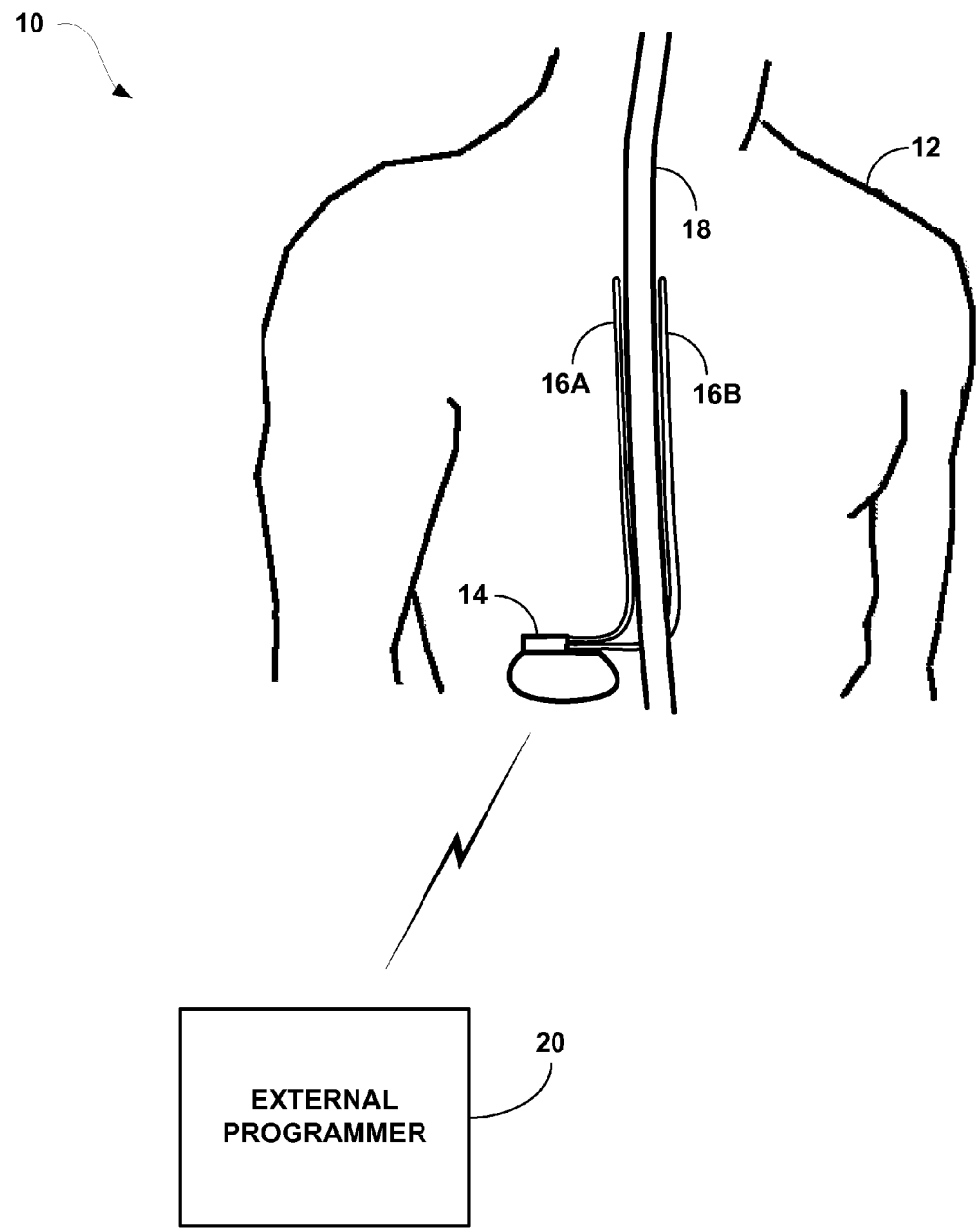
FIG. 1 is a conceptual diagram illustrating an implantable stimulation system including a pair of implantable stimulation leads, according to one embodiment.

In general, the disclosure provides electrical stimulators that include some electrical sources (e.g., current sources, voltage sources) that are directly connected to a plurality of electrode nodes, and other electrical sources that may be selectively connected to selected ones of the plurality of electrode nodes via a switching unit, such as a multiplexer. Each electrode node is connected or connectable to a respective one of a plurality of electrodes. An electrode node combination is a selected subset of the plurality of electrode nodes.

The electrodes may be located on one or more leads, such as implantable leads, coupled to one or more electrical stimulators. The techniques described in this disclosure also may be applicable to arrays of electrodes arranged on leads or on leadless stimulators, e.g., as surface electrodes on or protrusions from a device housing. The electrodes may be arranged in rows and/or columns (or other patterns), where a row or column may form an electrode array. As a further alternative, the electrodes may be arranged in rows and/or columns on paddle leads. A paddle lead may carry a two-dimensional array of electrodes arranged in rows and columns. Embodiments in which electrodes are located on leads may also include one or more electrodes on a housing of the stimulator.

The electrode combination also may specify the polarities of the electrodes in the selected subset. Electrodes with positive polarities are anodes, and may be coupled to positive electrical sources (e.g., current sources). Electrodes with negative polarities are cathodes, and may be coupled to negative electrical sources.

In general, an electrical stimulator may be an implantable stimulator or an external stimulator. In addition, the electrical stimulator may be a chronic stimulator intended for use over an extended period of time on the order of months or years. Alternatively, the electrical stimulator may be a trial stimulator intended for use over a shorter period on the order of days, weeks or months. The stimulator may deliver electrical stimulation therapy via one or more implantable leads that include electrodes for location proximate to target locations associated with the spinal cord, peripheral nerves, pelvic nerves, gastric nerves, or brain.

Stimulation may be used in different therapeutic applications, such as spinal cord stimulation (SCS), e.g., for pain, deep brain stimulation (DBS), cortical stimulation (CS), peripheral nerve stimulation (PNS), pelvic floor stimulation, gastric stimulation, and peripheral nerve field stimulation (PNFS). Stimulation may be configured to support therapy for a variety of symptoms, diseases and disorders, such as chronic pain, temporary pain, urinary incontinence, fecal incontinence, sexual dysfunction, gastro paresis, obesity, movement disorders, epilepsy, depression, anxiety, or the like.

In this disclosure, various techniques will be described in the context of electrical spinal cord or deep brain stimulation therapy for purposes of illustration, but without limitation as to application of such techniques to other target sites or therapy applications.

Chronic pain may be a debilitating condition for a patient. Pain may prevent the patient from performing certain activities, interacting with other people in social situations, or even sleeping regularly. Chronic pain may be the result of injury, disease, age, or other conditions. Pain may originate at organs, muscles, nerves, or other tissues, and most pain signals are transferred through the spinal cord. Electrical stimulation of certain nerves, nerve plexuses, or the spinal cord may provide an effective therapy for pain experienced by the patient. Stimulation of the brain may also be effective for alleviating pain, such as neuropathic or nociceptive pain. Stimulation of nerves, nerve plexuses, the spinal cord, and the brain may be referred to as neurostimulation or neuromodulation.

In some embodiments of this disclosure, an implantable electrical stimulator may be provided. The electrical stimulator may be a stimulator that delivers electrical stimulation to, for example, a portion of the spinal cord to block pain signals being transferred to the brain of the patient. In some cases, electrical stimulation may permanently reduce chronic pain. In general, an electrode combination or configuration defines a selected set of electrodes on one lead or across multiple leads, as well as the polarities of the individual electrodes, and hence the formation of cathodes and anodes with the set of electrodes. Although primarily described herein with reference to stimulation delivered as pulses, embodiments of the invention may deliver or control delivery of stimulation in the form of continuous time signals or other types of waveforms.

An external programmer that accepts parameter-directed user input to indicate shifting of electrode combinations may provide a quick and simple interface that permits a patient or other use to change electrode combinations in an effort to maintain or improve therapeutic efficacy. A group may refer to a group of programs that may be delivered simultaneously or on an interleaved basis. A program refers to a set of stimulation parameters, which may include amplitude, pulse width, pulse rate, and electrode combination. Again, an electrode combination may indicate selected electrodes and associated polarities for delivery of stimulation therapy.

In one embodiment, an electrical stimulator includes a plurality of electrode nodes connected or connectable to a plurality of electrodes. The electrical stimulator is capable of selectively connecting at least one positive electrical source (e.g., current source, voltage source) of the stimulator to a selected one or more of the plurality of electrode nodes to configure one or more associated electrodes as anodes within one or more electrode combinations. In such fashion, multiple anodes may share and be multiplexed with the at least one positive electrical source, rather than each being connected to a separate positive electrical source. Reducing the number of positive electrical sources that are connected to anodes within an implantable stimulator may thereby help reduce the number of electrical components in and battery consumption of the electrical stimulator. In various cases, tissue activation during electrical stimulation may occur at the cathodes that are coupled to the stimulator. Thus, in these cases, each electrode node is directly connected to a negative electrical source, so that each electrode may be independently configured as a cathode.

FIG. 1 is a conceptual diagram illustrating an implantable stimulation system 10 including a pair of implantable electrode arrays in the form of stimulation leads. As shown in FIG. 1, system 10 includes an implantable stimulator 14 and external programmer 20 shown in conjunction with a patient 12. Although FIG. 1 shows implantable stimulator 14, techniques described in this disclosure may be applied to external stimulators. Stimulation energy is delivered from stimulator 14 to spinal cord 18 of patient 12 via one or more electrodes of implantable leads 16A and 16B (collectively "leads 16"). In some applications, such as spinal cord stimulation (SCS), the adjacent implantable leads 16 may have longitudinal axes that are substantially parallel to one another.

Although deployment of electrodes via leads 16 will be described for purposes of illustration, arrays of electrodes could be deployed in different ways. For example, a housing associated with a leadless stimulator may carry arrays of electrodes, e.g., rows and/or columns (or other patterns). Such electrodes may be arranged as surface electrodes, ring electrodes, or protrusions. As a further alternative, electrode arrays may be formed by rows and/or columns of electrodes on one or more paddle leads. In some embodiments, electrode arrays may include electrode segments, which may be arranged at respective positions around a periphery of a lead, e.g., arranged in the form of one or more segmented rings around a circumference of a cylindrical lead. Furthermore, although not illustrated in FIG. 1, some embodiments may include one or more electrodes on the housing of stimulator 14 in addition to the electrodes on leads 16.

In the example of FIG. 1, leads 16 carry electrodes that are placed adjacent to the target tissue of the spinal cord. Leads 16 may be implanted and coupled to an implanted stimulator 14. Alternatively, in some embodiments, leads 16 may be implanted and coupled to an external stimulator, e.g., through a percutaneous port. In additional embodiments, stimulator 14 may be a leadless stimulator with one or more arrays of electrodes arranged on a housing of the stimulator rather than leads that extend from the housing. Application of certain techniques will be described herein with respect to implantable stimulator 14 and implantable leads 16 with ring electrodes for purposes of illustration.

In the example of FIG. 1, stimulation energy is delivered to the spinal cord 18 to reduce the amount of pain perceived by patient 12. As mentioned above, however, the stimulator may be used with a variety of different pain therapies, such as peripheral nerve stimulation (PNS), peripheral nerve field stimulation (PNFS), deep brain stimulation (DBS), cortical stimulation (CS), pelvic floor stimulation, gastric stimulation, and the like. The stimulation delivered by stimulator 14 may take the form of stimulation pulses or continuous stimulation waveforms, and may be characterized by controlled voltage levels or controlled current levels, as well as pulse width and pulse rate in the case of stimulation pulses.

Moreover, the stimulation may be delivered via selected combinations of electrodes carried by one or both of leads 16. The target tissue may be any tissue affected by electrical stimulation energy, such as electrical stimulation pulses or waveforms. Such tissue includes nerves, smooth muscle, and skeletal muscle. In the example illustrated by FIG. 1, the target tissue is spinal cord 18. Stimulation of spinal cord 18 may, for example, prevent pain signals from traveling through the spinal cord and to the brain of the patient. Patient 12 perceives the interruption of pain signals as a reduction in pain and, therefore, efficacious therapy.

With reference to FIG. 1, a user, such as a clinician or patient 12, may interact with a user interface of external programmer 20 to program stimulator 14. Programming of stimulator 14 may refer generally to the generation and transfer of commands, programs, or other information to control the operation of the stimulator. For example, programmer 20 may transmit programs, parameter adjustments, program selections, group selections, or other information to control the operation of stimulator 14, e.g., by wireless telemetry. As one example, programmer 20 may transmit parameter adjustments to support parameter-directed shifting of electrode combinations used to deliver stimulation according to a selected program.

In some cases, external programmer 20 may be characterized as a physician or clinician programmer if it is primarily intended for use by a physician or clinician. In other cases, external programmer 20 may be characterized as a patient programmer if it is primarily intended for use by a patient. In general, a physician or clinician programmer may support selection and generation of programs by a clinician for use by stimulator 14, whereas a patient programmer may support adjustment and selection of such programs by a patient during ordinary use.

Stimulator 14 may be implanted in patient 12 at a location minimally noticeable to the patient. Alternatively, stimulator may be external with percutaneously implanted leads. For SCS, stimulator 14 may be located in the lower abdomen, lower back, or other location to secure the stimulator. Leads 16 are tunneled from stimulator 14 through tissue to reach the target tissue adjacent to spinal cord 18 for stimulation delivery. At the distal ends of leads 16 are one or more electrodes (not shown) that transfer the stimulation pulses from the lead to the tissue. The electrodes may be electrode pads on a paddle lead, circular (i.e., ring) electrodes surrounding the body of leads 16, conformable electrodes, cuff electrodes, segmented electrodes, or any other type of electrodes capable of forming unipolar, bipolar or multi-polar electrode configurations. In general, ring electrodes arranged at different axial positions at the distal ends of leads 16 will be described for purposes of illustration.

In one embodiment, stimulator 14 includes a plurality of electrode nodes connected or connectable to a plurality of electrodes. Stimulator 14 is capable of selectively connecting at least one positive electrical source (e.g., current source, voltage source) of stimulator 14 to a selected one or more of the plurality of electrode nodes to configure one or more associated electrodes of leads 16 as anodes within one or more electrode combinations. In such fashion, multiple anodes may share and be multiplexed with the at least one positive electrical source, rather than each being connected to a separate positive electrical source, as will be described in more detail below. Reducing the number of positive electrical sources that are connected to anodes within implantable stimulator 14 may thereby help reduce the number of electrical components in and battery consumption of electrical stimulator 14. In various cases, tissue activation during electrical stimulation may occur at the cathodes that are coupled to stimulator 14. Thus, in these cases, each electrode node may be directly connected to a negative electrical source, so that each electrode may be independently configured as a cathode.

Figure 2:
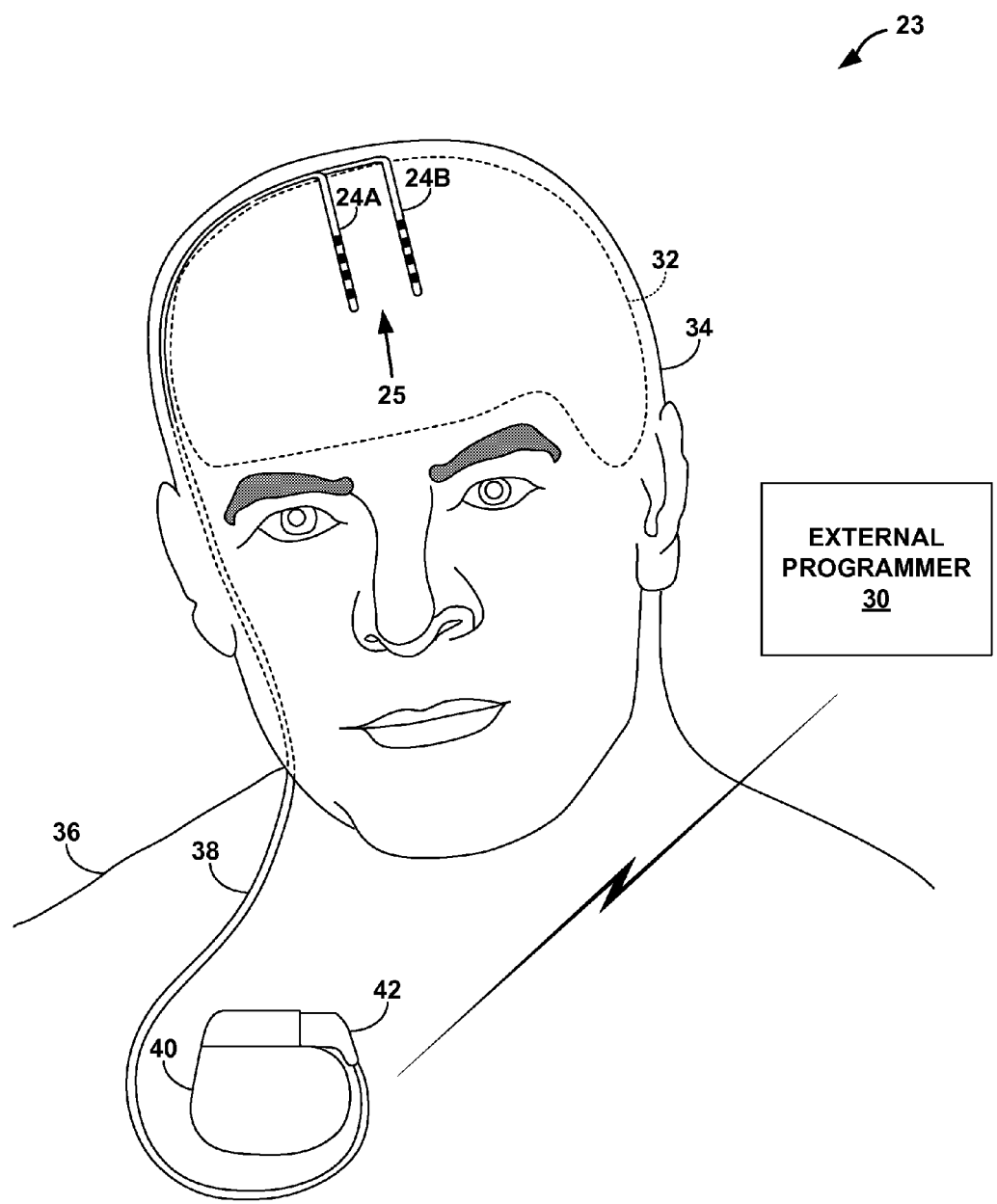
FIG. 2 is a conceptual diagram illustrating an implantable deep brain stimulation (DBS) system, according to one embodiment.

FIG. 2 is a conceptual diagram illustrating an example DBS system 23, which includes implantable medical device (IMD) 40, lead extension 38, leads 24A and 24B, and electrode array 25. IMD 40 includes a therapy module that delivers electrical stimulation therapy to patient 36 via electrode array 25 provided by leads 24A and 24B.

IMD 40 is implanted in patient 36. Implanted lead extension 38 is coupled to IMD 40 via connector 42. Lead extension 38 traverses from the implant site of IMD 40 within a chest cavity of patient 36, and along the neck of patient 36 to cranium 34 of patient 36 to access brain 32. Leads 24A and 24B (collectively "leads 24") are implanted within the right and left hemispheres, respectively, of patient 36 in order deliver electrical stimulation to one or more regions of brain 32, which may be selected based on the patient condition or disorder controlled by DBS system 23. Electrode array 25 includes a plurality of electrodes carried by leads 24. External programmer 30 wireless communicates with IMD 40 as needed to provide or retrieve therapy information. While patient 36 is generally referred to as a human patient, other mammalian or non-mammalian patients are also contemplated.

Although leads 24 are shown in FIG. 2 as being coupled to a common lead extension 38, in other embodiments, leads 24 may be coupled to IMD 40 via separate lead extensions or directly to the therapy module. Leads 24 may deliver electrical stimulation from IMD 40 to brain 32 via selected combinations of the electrodes of electrode array 25 to treat any number of neurological disorders or diseases. Example neurological disorders may include depression, dementia, obsessive-compulsive disorder, and movement disorders, such as Parkinson's disease, spasticity, and epilepsy. DBS is also useful for treating other patient conditions, such as migraines and obesity. IMD 40 may include a housing electrode (not shown), which may be used by IMD 40 in combination with any of the electrodes of electrode array 25 for delivery of stimulation.

Leads 24 may be implanted within a desired location of brain 32 through respective holes in cranium 34. Leads 24 may be placed at any location within brain 32 such that the electrodes of electrode array 25 are capable of providing electrical stimulation to targeted tissue during treatment. Electrical stimulation generated from the signal generator (not shown) within the therapy module of IMD 40 may be configured to treat a variety of disorders and conditions. Example locations for electrode array 25 within brain 32 may include the pedunculopontine nucleus (PPN), thalamus, basal ganglia structures (e.g., globus pallidus, substantia nigra, subthalamic nucleus), zona inserta, fiber tracts, lenticular fasciculus (and branches thereof), ansa lenticularis, and/or the Field of Forel (thalamic fasciculus). In the case of migraines, electrode array 25 may be implanted to provide stimulation to the visual cortex of brain 32 in order to reduce or eliminate migraine headaches afflicting patient 36. However, the target therapy delivery site may depend upon the patient condition or disorder being treated.

The electrodes of leads 24 are shown as ring electrodes. Ring electrodes are commonly used in DBS applications because they are simple to program and are capable of delivering an electrical field to any tissue adjacent to leads 24. In other embodiments, the electrodes of leads 24 may have different configurations. For examples, the electrodes of leads 24 may have a complex electrode array geometry that is capable of producing shaped electrical fields. The complex electrode array geometry may include multiple electrodes (e.g., partial ring or segmented electrodes) around the perimeter of each lead 24, rather than one ring electrode. In this manner, electrical stimulation may be directed to a specific direction from leads 24 to enhance therapy efficacy and reduce possible adverse side effects from stimulating a large volume of tissue. In some embodiments, a housing of IMD 40 may include one or more stimulation and/or sensing electrodes. In alternative examples, leads 24 may be have shapes other than elongated cylinders as shown in FIG. 2. For example, leads 24 may be paddle leads, spherical leads, bendable leads, or any other type of shape effective in treating patient 36.

IMD 40 includes a therapy module that generates the electrical stimulation delivered to patient 36 via leads 24. A signal generator (not shown), within IMD 40 produces the stimulation in the manner defined by the therapy parameters selected by the clinician and/or patient 36. Generally the signal generator is configured to produce electrical pulses to treat patient 36. However, the signal generator of IMD 40 may be configured to generate a continuous wave signal, e.g., a sine wave or triangle wave. In either case, IMD 40 generates the electrical stimulation therapy for DBS according to therapy parameters selected at that given time in therapy.

In the embodiment shown in FIG. 2, IMD 40 generates the electrical stimulation according to one or more therapy parameters, which may be arranged in a therapy program (or a parameter set). The therapy program includes a value for a number of parameters that define the stimulation. For example, the therapy parameters may include voltage or current pulse amplitudes, pulse widths, pulse rates, pulse frequencies, electrode combinations, and the like. IMD 40 may store a plurality of programs. During a trial stage in which IMD 40 is evaluated to determine whether IMD 40 provides efficacious therapy to patient 36, the stored programs may be tested and evaluated for efficacy. During chronic therapy in which IMD 40 is implanted within patient 36 for delivery of therapy on a non-temporary basis, patient 36 may select the programs for delivering therapy. For example, the different programs may provide more efficacious therapy during different activities, different times of the day, and so forth. Thus, patient 36 may modify the value of one or more parameters within a single given program or switch between programs in order to alter the efficacy of the therapy as perceived by patient 36.

IMD 40 may include a memory to store one or more therapy programs, instructions defining the extent to which patient 36 may adjust therapy parameters, switch between programs, or undertake other therapy adjustments. Patient 36 may generate additional programs for use by IMD 40 via external programmer 30 at any time during therapy or as designated by the clinician. If patient 36 modifies a therapy program, patient 36 may provide input to therapy system 23 that causes the therapy module within IMD 40 to save the parameters as a new therapy program for later use.

Generally, IMD 40 is constructed of a biocompatible material that resists corrosion and degradation from bodily fluids. For example, IMD 40 may include a housing constructed of such material(s), which houses the various components of IMD 40, and may be hermetically sealed. IMD 40 may be implanted within a subcutaneous pocket close to the stimulation site. Although IMD 40 is implanted within a chest cavity of patient 36 in the embodiment shown in FIG. 2, in other embodiments, IMD 40 may be implanted within cranium 34. While IMD 40 is shown as implanted within patient 36 in FIG. 2, in other embodiments, IMD 40 may be located external to the patient. For example, IMD 40 may be a trial stimulator electrically coupled to leads 24 via a percutaneous lead during a trial period. If the trial stimulator indicates therapy system 23 provides effective treatment to patient 36, the clinician may implant a chronic stimulator within patient 36 for long term treatment.

Programmer 30 is an external computing device that the user, i.e., the clinician and/or patient 36, uses to communicate with IMD 40. For example, programmer 30 may be a clinician programmer that the clinician uses to communicate with IMD 40. Alternatively, programmer 30 may be a patient programmer that allows patient 36 to view and modify therapy parameters. The clinician programmer may include more programming feature than the patient programmer. In other words, more complex or sensitive tasks may only be allowed by the clinician programmer to prevent the untrained patient from making undesired changes to IMD 40.

Programmer 30 may be a hand-held computing device with a display viewable by the user and a user input mechanism that can be used to provide input to programmer 30. For example, programmer 30 may include a small display screen (e.g., a liquid crystal display or a light emitting diode display) that provides information to the user. In addition, programmer 30 may include a keypad, buttons, a peripheral pointing device or another input mechanism that allows the user to navigate though the user interface of programmer 30 and provide input. If programmer 40 includes buttons and a keypad, the buttons may be dedicated to performing a certain function, i.e., a power button, or the buttons and the keypad may be soft keys that change in function depending upon the section of the user interface currently viewed by the user. Alternatively, the screen (not shown) of programmer 30 may be a touch screen that allows the user to provide input directly to the user interface shown on the display. The user may use a stylus or their finger to provide input to the display. In other embodiments, programmer 30 may be a larger workstation or a separate application within another multi-function device. For example, the multi-function device may be a cellular phone or personal digital assistant that can be configured to an application to simulate programmer 30. Alternatively, a notebook computer, tablet computer, or other personal computer may enter an application to become programmer 30 with a wireless adapter connected to the personal computer for communicating with IMD 40.

When programmer 30 is configured for use by the clinician, programmer 30 may be used to transmit initial programming information to IMD 40. This initial information may include system 23 hardware information such as the type of leads 24 and the electrode arrangement, the position of leads 24 within brain 32, the configuration of electrode array 25, initial programs having therapy parameters, and any other information the clinician desires to program into IMD 40. Programmer 30 may also be capable of completing any functional tests (e.g., measuring the impedance of electrodes 26 or the electrodes of leads 24A and 24B) the clinician desires to complete before starting therapy and sending patient 36 home.

The clinician also uses programmer 30 to program IMD 40 with initial stimulation programs, defined as programs that define the therapy delivered by IMD 40. During a programming session, the clinician may determine one or more therapy programs that may provide effective therapy to patient 36. Patient 36 may provide feedback to the clinician as to the efficacy of the specific program being evaluated. Once the clinician has identified one or more programs that may be beneficial to patient 36, patient 36 may continue the evaluation process and determine which program best alleviates the condition of patient 36. Programmer 30 may assist the clinician in the creation/identification of therapy programs by providing a methodical system of identifying potentially beneficial therapy parameters.

Programmer 30 may also be configured for use by patient 36. When configured as the patient programmer, programmer 30 may have limited functionality in order to prevent patient 36 from altering critical functions or applications that may be detrimental to patient 36. In this manner, programmer 30 may only allow patient 36 to adjust certain therapy parameters or set an available range for a particular therapy parameter.

Whether programmer 30 is configured for clinician or patient use, programmer 30 may communicate to IMD 40 or any other computing device via wireless communication. Programmer 30, for example, may communicate via wireless communication with IMD 40 using radio frequency (RF) telemetry techniques known in the art. Programmer 30 may also communicate with another programmer or computing device via a wired or wireless connection using any of a variety of local wireless communication techniques, such as RF communication according to the 802.11 or Bluetooth specification sets, infrared communication according to the IRDA specification set, or other standard or proprietary telemetry protocols. Programmer 30 may also communicate with another programming or computing device via exchange of removable media, such as magnetic or optical disks, or memory cards or sticks. Further, programmer 30 may communicate with IMD 40 and other another programmer via remote telemetry techniques known in the art, communicating via a local area network (LAN), wide area network (WAN), public switched telephone network (PSTN), or cellular telephone network, for example.

In one embodiment, IMD 40 includes a plurality of electrode nodes within its biocompatible housing and connected or connectable to the plurality of electrodes of electrode array 25. IMD 40 is capable of selectively connecting at least one positive electrical source (e.g., current source, voltage source) of IMD 40 to a selected one or more of the plurality of electrode nodes to configure one or more associated electrodes of array 25 as anodes within one or more electrode combinations. In such fashion, multiple anodes may share and be multiplexed with the at least one positive electrical source, rather than each being connected to a separate positive electrical source, as will be described in more detail below. Reducing the number of positive electrical sources that are connected to anodes within implantable IMD 40 may thereby help reduce the number of electrical components in and battery consumption of IMD 40. In various cases, tissue activation during electrical stimulation may occur at the cathodes that are coupled to IMD 40. Thus, in these cases, each electrode node may be directly connected to a negative electrical source, so that each electrode of array 25 may be independently configured as a cathode.

Figure 3:
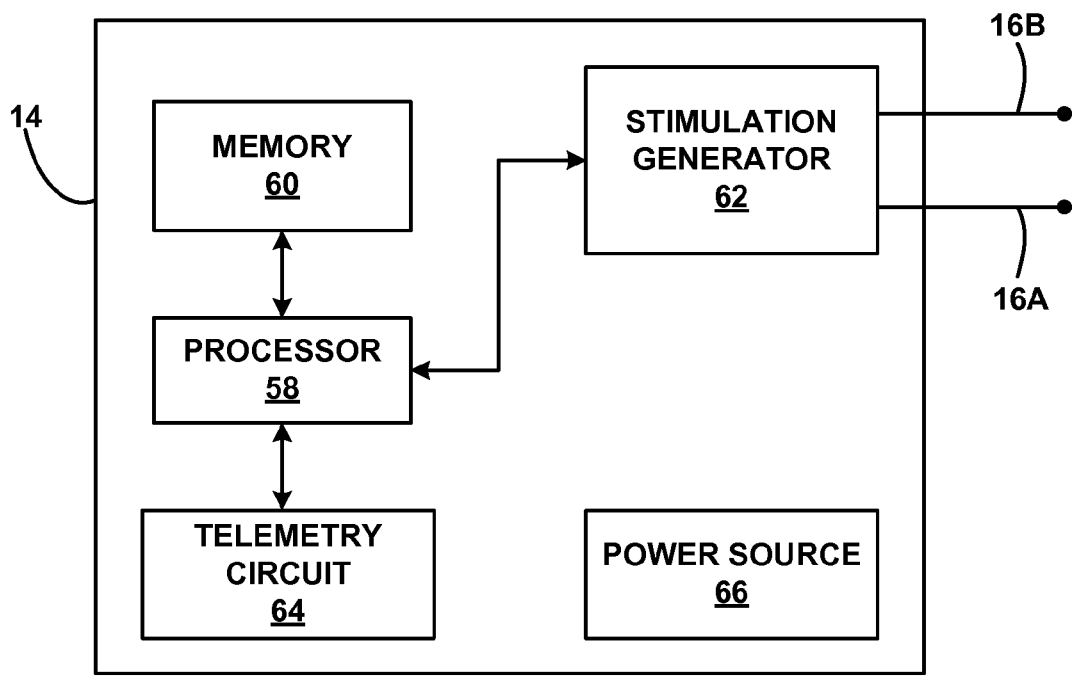
FIG. 3 is a functional block diagram illustrating various components of an implantable electrical stimulator, according to one embodiment.

FIG. 3 is a functional block diagram illustrating various components of implantable stimulator 14 shown in FIG. 1. Although the components shown in the example of FIG. 3 are described in reference to implantable stimulator 14, these same components may also be included within IMD 40 shown in FIG. 2 and used within system 23.

In the example of FIG. 3, stimulator 14 includes a processor 58, memory 60, stimulation signal generator 62, telemetry circuit 64, and power source 66. Memory 60 may store instructions for execution by processor 58, stimulation therapy data, efficacy feedback, and any other information regarding therapy or patient 12. Therapy information may be recorded for long-term storage and retrieval by a user, and adjustment of the program path of the therapeutic tree. Memory 60 may include separate memories for storing instructions, the therapeutic tree, program path, and program histories.

Processor 58 controls stimulation generator 62 to deliver electrical stimulation via electrode combinations formed by electrodes in one or more electrode arrays. For example, stimulation generator 62 may deliver electrical stimulation therapy via electrodes on one or more leads 16, e.g., as stimulation pulses or continuous waveforms. Stimulation generator 62 may include stimulation generation circuitry to generate stimulation pulses or waveforms and switching circuitry to switch the stimulation across different electrode combinations, e.g., in response to control by processor 58. In particular, processor 58 may control the switching circuitry on a selective basis to cause stimulation generator 62 to deliver electrical stimulation to selected electrode combinations.

When activating stimulation, processor 58 may access not only the memory location specifying the electrode combination but also other memory locations specifying various stimulation parameters such as voltage or current amplitude, pulse width and pulse rate. Stimulation generator 62, e.g., under control of processor 58, then makes use of the electrode combination and parameters in formulating and delivering the electrical stimulation to the patient. Processor 58 also may control telemetry circuit 64 to send and receive information. For example, telemetry circuit 64 may send information to and receive information from an external device, such as programmer 20. An exemplary range of electrical stimulation parameters likely to be effective in treating chronic pain, e.g., when applied to spinal cord 18, are listed below. While stimulation pulses are described, stimulation signals may be of any of a variety of forms such as sine waves or the like.

1. Pulse Rate: between approximately 0.5 Hz and 1200 Hz, more preferably between approximately 5 Hz and 250 Hz, and still more preferably between approximately 30 Hz and 130 Hz.

2. Amplitude: between approximately 0.1 volts and 50 volts, more preferably between approximately 0.5 volts and 20 volts, and still more preferably between approximately 1 volt and 10 volts. In other embodiments, a current amplitude may be defined as the biological load in the voltage that is delivered. For example, the range of current amplitude may be between 0.1 milliamps (mA) and 50 mA.

3. Pulse Width: between about 10 microseconds and 5000 microseconds, more preferably between approximately 100 microseconds and 1000 microseconds, and still more preferably between approximately 180 microseconds and 450 microseconds.

Processor 58 stores stimulation parameters in memory 60, e.g., as programs and groups of programs. Upon selection of a particular program group, processor 58 may control stimulation generator 62 to deliver stimulation according to the programs in the groups, e.g., simultaneously or on a time-interleaved basis. A group may include a single program or multiple programs. As mentioned previously, each program may specify a set of stimulation parameters, such as amplitude, pulse width and pulse rate. In addition, each program may specify a particular electrode combination for delivery of stimulation. Again, the electrode combination may specify particular electrodes in a single array or multiple arrays, and on a single lead or among multiple leads.

Wireless telemetry in stimulator 14 with external programmer 20 or another device may be accomplished by radio frequency (RF) communication or proximal inductive interaction of stimulator 14 with external programmer 20. Telemetry circuit 64 may send information to and receive information from external programmer 20 on a continuous basis, at periodic intervals, or upon request from the stimulator or programmer. To support RF communication, telemetry circuit 64 may include appropriate electronic components, such as amplifiers, filters, mixers, encoders, decoders, and the like.

Power source 66 delivers operating power to the components of stimulator 14. Power source 66 may include a small rechargeable or non-rechargeable battery and a power generation circuit to produce the operating power. Recharging may be accomplished through proximal inductive interaction between an external charger and an inductive charging coil within stimulator 14. In some embodiments, power requirements may be small enough to allow stimulator 14 to utilize patient motion and implement a kinetic energy-scavenging device to trickle charge a rechargeable battery. In other embodiments, traditional batteries may be used for a limited period of time. As a further alternative, an external inductive power supply could transcutaneously power stimulator 14 when needed or desired.

As described previously, in one embodiment, stimulator 14 is capable of selectively connecting at least one positive electrical source (e.g., current source, voltage source) contained within stimulation generator 62 to a selected one or more of a plurality of electrode nodes that may each then be coupled to anodes within one or more of leads 16A and 16B. In such fashion, multiple anodes may share and be multiplexed with the at least one positive electrical source, rather than each being connected to a separate positive electrical source. Processor 58 may control one or more switching units within stimulation generator 62 to connect the at least one positive electrical source to the selected one or more electrode nodes. Each electrode node connected to a cathode may be independently coupled to a negative electrical source within stimulation generator 62, as described in more detail below.

Reducing the number of positive electrical sources within stimulation generator 62 that are connected to anodes within implantable stimulator 14 may thereby help reduce the number of electrical components in stimulation generator 62 (e.g., number of transistors) and power consumption of power source 66, due to a reduced number of positive electrical sources.

Figure 4:
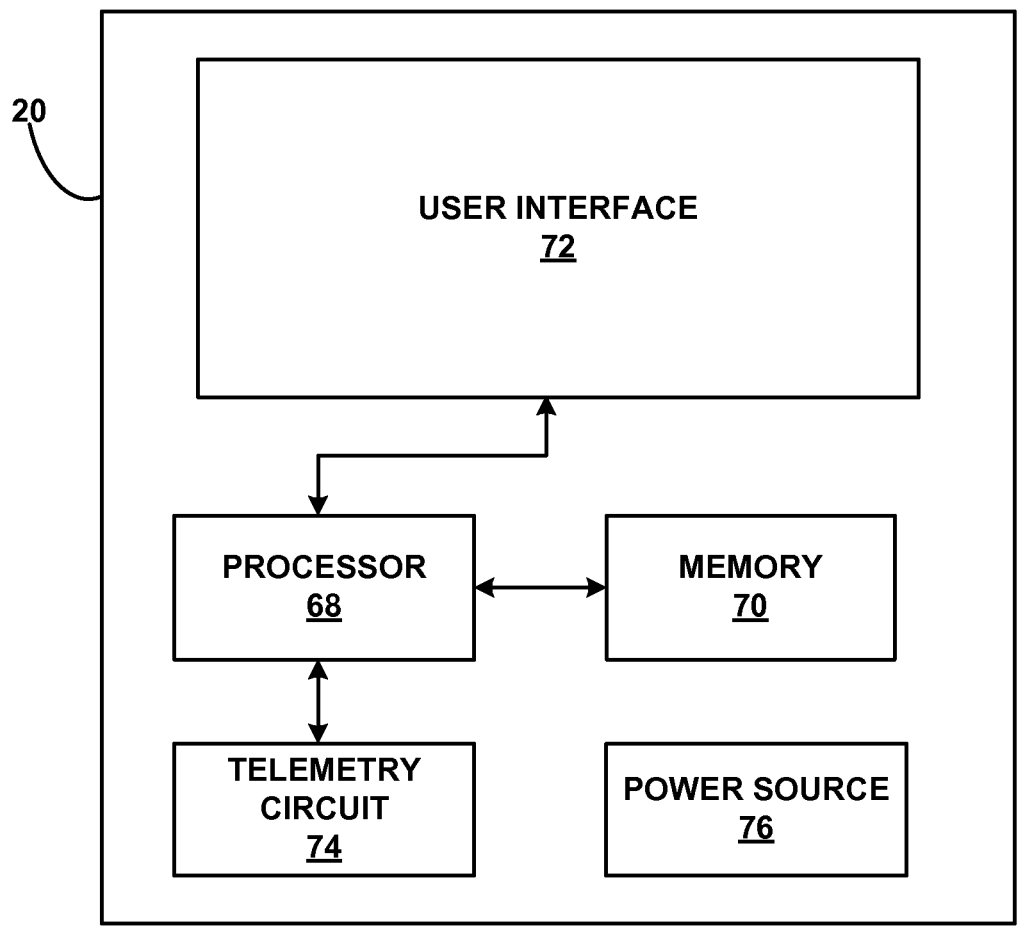
FIG. 4 is a functional block diagram illustrating various components of an external programmer for an implantable stimulator, according to one embodiment.

FIG. 4 is a functional block diagram illustrating various components of an external programmer 20 for an implantable stimulator 14. As shown in FIG. 4, external programmer 20 includes processor 68, memory 70, telemetry circuit 74, user interface 72, and power source 76. A clinician or patient 12 interacts with user interface 72 in order to, for example, manually select, change or modify programs, adjust voltage or current amplitude, provide efficacy feedback, or view stimulation data.

User interface may include a screen and one or more input buttons, as shown in FIG. 2, that allow external programmer 20 to receive input from a user. As shown in FIG. 2, the screen may be a liquid crystal display (LCD), dot matrix display, or touch screen. The input buttons may include a touch pad, increase and decrease buttons, emergency shut off button, and other buttons needed to control the stimulation therapy, as described above with regard to FIG. 2. Processor 68 controls user interface 72, retrieves data from memory 70 and stores data within the memory. Processor 68 also controls the transmission of data through telemetry circuit 74 to stimulator 14. Memory 70 includes operation instructions for processor 68.

Telemetry circuit 74 allows the transfer of data to and from stimulator 14. Telemetry circuit 74 may communicate automatically with stimulator 14 at a scheduled time or when the telemetry circuit detects the proximity of the stimulator. Alternatively, telemetry circuit 74 may communicate with stimulator 14 when signaled by a user through user interface 72. To support RF communication, telemetry circuit 74 may include appropriate electronic components, such as amplifiers, filters, mixers, encoders, decoders, and the like. Power source 76 may be a rechargeable battery, such as a lithium ion or nickel metal hydride battery. Other rechargeable or conventional batteries may also be used. In some cases, external programmer 20 may be used when coupled to an alternating current (AC) outlet, i.e., AC line power, either directly or via an AC/DC adapter.

Figure 5:
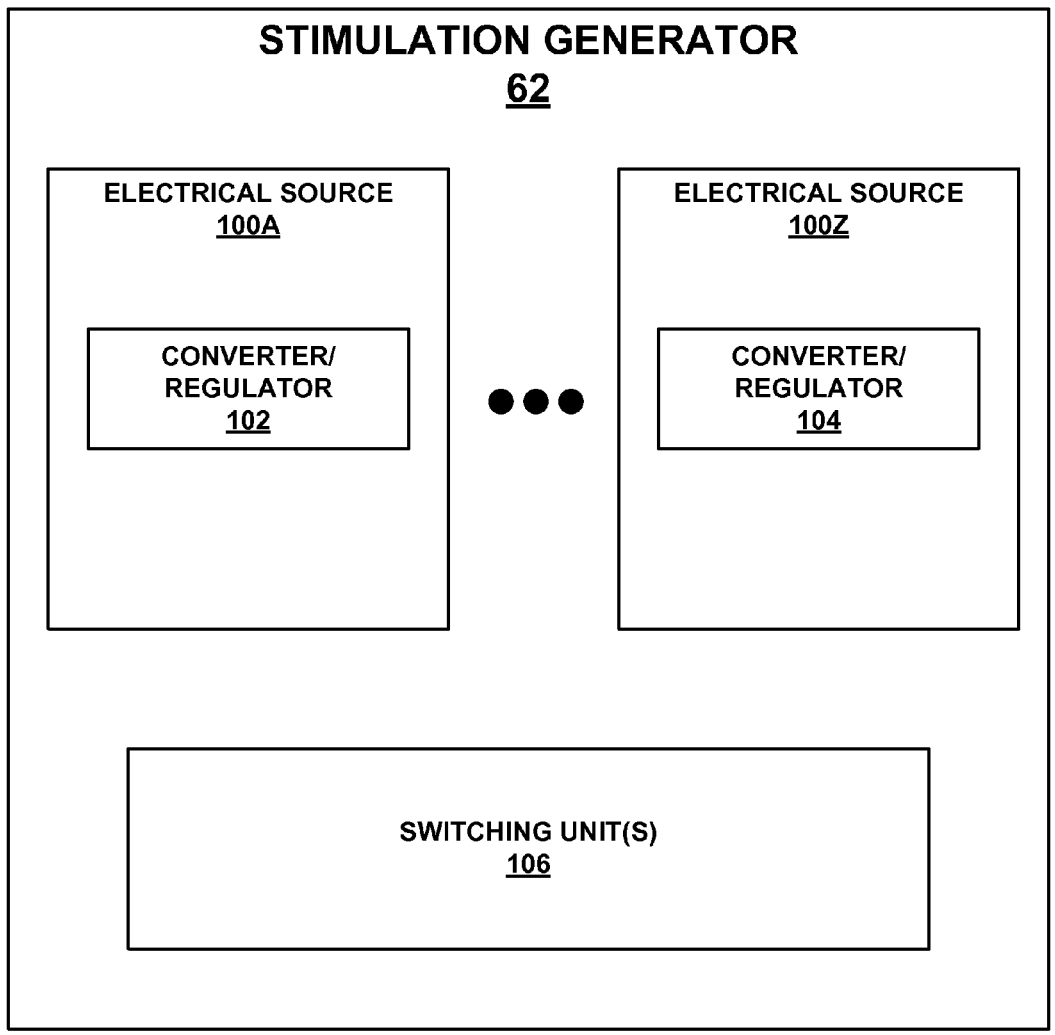
FIG. 5 is a block diagram illustrating additional details of the stimulation generator shown in FIG. 3, according to one embodiment.

FIG. 5 is a block diagram illustrating additional details of stimulation generator 62 shown in FIG. 3, according to one embodiment. Although the stimulation generator shown in the example of FIG. 5 is part of stimulator 14, it may also, in some embodiments, be part of IMD 40 shown in FIG. 2.

Stimulation generator 62 includes one or more electrical sources 100A-100Z. In some embodiments, each electrical source 100A-100Z may comprise a current or a voltage source that is capable of delivering electrical energy. Electrical sources 100A-100Z may include positive electrical sources (which deliver electrical stimulation having a positive polarity) and/or negative electrical sources (which deliver electrical stimulation having a negative polarity).

Each electrical source 100A-100Z includes a converter and/or a regulator. For example, as shown in FIG. 5, electrical source 100A includes a converter/regulator 102 (which may include a converter and/or a regulator), while electrical source 100Z includes a converter/regulator 104. In some embodiments, converter/regulators 102 and 104 may comprise a DAC (digital-to-analog converter) and/or a voltage regulator. For example, if electrical source 100A comprises a current source, converter/regulator 102 may comprise a DAC. If electrical source 100Z comprises a voltage source, converter/regulator 104 may comprise a voltage regulator. Each converter/regulator 102, 104 is capable of converting or regulating signals that are received from processor 58 (FIG. 3), power source and/or other components of stimulator 16, such as a capacitor array, into a stimulation signal with the desired signal parameters, e.g., desired amplitude.

One or more of electrical sources 100A-100Z may be coupled to one or more switching units 106. Switching units 106 may comprise a plurality of electrical switches, or a switching matrix, to connect electrical sources 100A-100Z to one or more electrodes that are coupled to stimulation generator. In one embodiment, switching units 106 may comprise one or more multiplexers. One or more of electrical sources 100 may not be connected to switching units 106, according to some embodiments.

Stimulation generator 62 is capable of selectively connecting at least one positive electrical source contained within electrical sources 100A-100Z to a selected one or more of a plurality of electrode nodes such that associated electrodes may function as anodes within one or more electrode combinations. In such fashion, multiple anodes may share the at least one positive electrical source, rather than each being connected to a separate positive electrical source. Each electrode node that is connected to a cathode may be independently coupled to a negative electrical source within stimulation generator 62, as described in more detail below.

Figure 6:
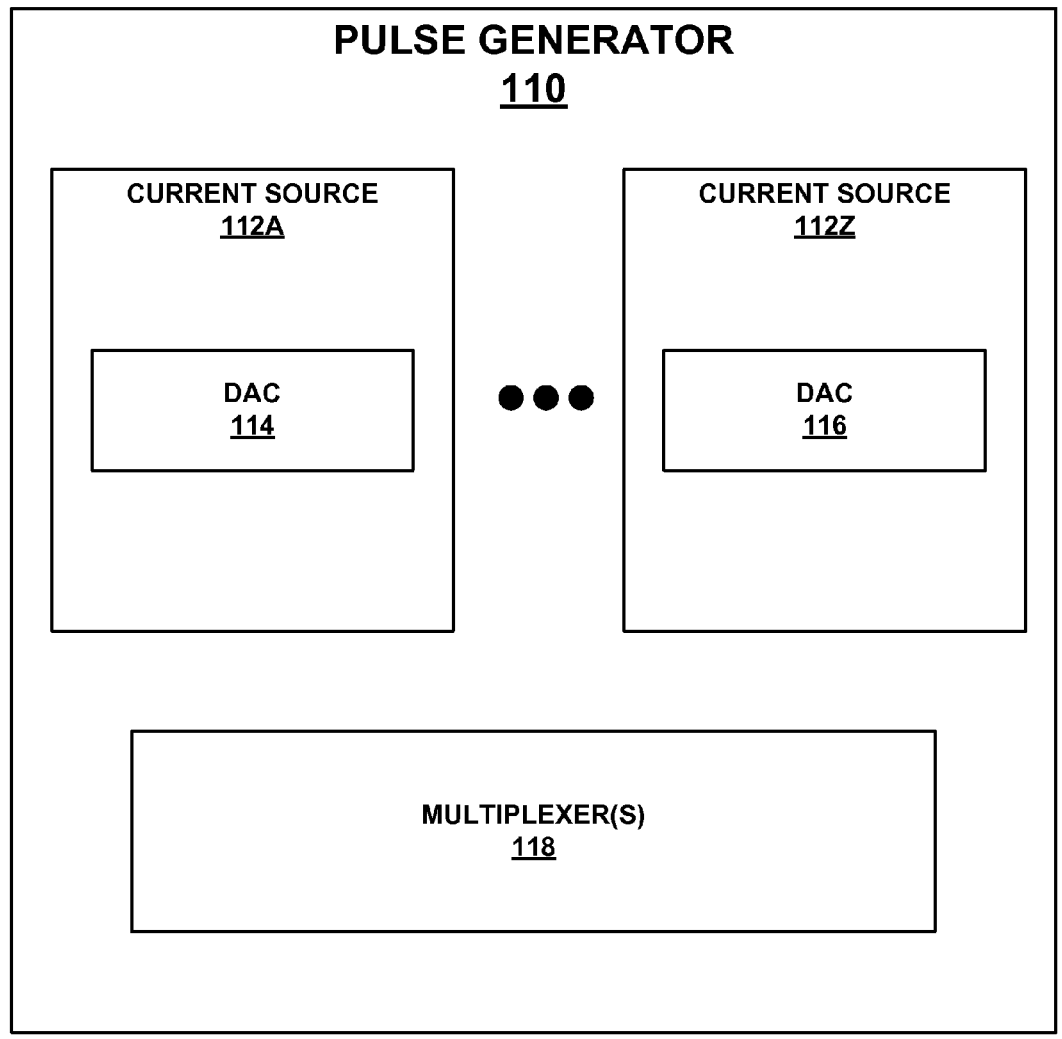
FIG. 6 is a block diagram illustrating an example of a pulse generator, according to one embodiment.

FIG. 6 is a block diagram illustrating an example of a pulse generator 110, according to one embodiment. In this embodiment, stimulation generator 62 shown in FIG. 5 may comprise pulse generator 110 shown in FIG. 6. Pulse generator 110 is capable of generating and delivering electrical stimulation to one or more electrodes via electrode nodes in the form of electrical pulses.

As shown in FIG. 6, pulse generator 110 includes one or more current sources 112A-112Z. Each current source 112A-112Z is capable of generating and providing electrical current, such as in the form of current pulses. In some embodiments, each current source 112A-112Z may be configured to deliver current having a positive polarity (positive current source) or having a negative polarity (negative current source). Each current source 112A-112Z includes a digital-to-analog converter (DAC). For example, current source 112A includes DAC 114, and current source 112Z includes DAC 116. Each DAC 114 and 116 may convert digital control signals provided by processor 58 (FIG. 3) into analog current signals that may then be delivered to one or more electrodes.

Current sources 112A-112Z are each coupled to one or more multiplexers 118. Multiplexers 118 are coupled to one or more electrode nodes that are connected to one or more electrodes, such as electrodes associated with leads 16A and 16B (FIG. 3), for example. Multiplexers 118 may include one or more switching circuits to connect each current source 112A-112Z to one or more electrode nodes. Multiplexers 118 may be controlled, in some embodiments, by processor 58. In these embodiments, processor 58 may provide one or more control signals to multiplexers 118 to control which current sources 112A-112Z are coupled to which electrode nodes.

Pulse generator 110 is capable of selectively connecting at least one positive current source contained within current sources 112A-112Z to a selected one or more of a plurality of electrode nodes that are connected to one or more anodes within at least one electrode combination. In such fashion, multiple anodes may share the at least one positive current source, rather than each being connected to a separate positive current source. Each electrode node connected to a cathode may be independently coupled to a negative current source within current sources 112A-112Z.

Figure 7:
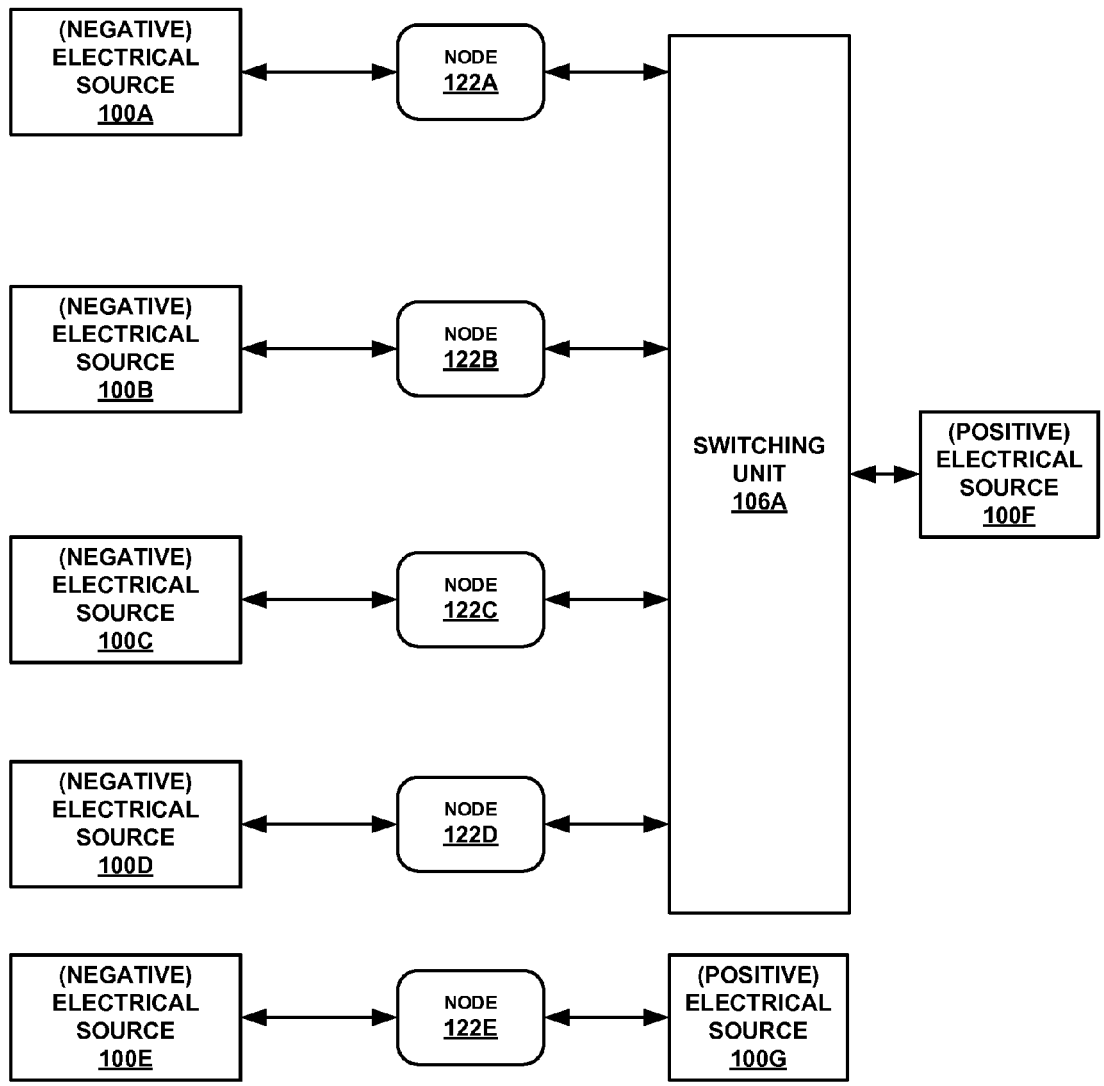
FIG. 7 is a block diagram illustrating an example configuration in which a switching unit of the stimulation generator shown in FIG. 5 may connect a positive electrical source to a selected one of a plurality of electrode nodes, and in which negative electrical sources are directly connected to respective electrode nodes, according to one embodiment.

FIG. 7 is a block diagram illustrating an example configuration in which a switching unit 106A of stimulation generator 62 shown in FIG. 5 may connect a positive electrical source 100F to a selected one of electrode nodes 122A-122D, according to one embodiment. In this embodiment, switching unit 106A may be included within the one or more switching units 106 shown in FIG. 5. Positive electrical source 100F may be one of the electrical sources in 100A-100Z (FIG. 5) that is configured to deliver electrical energy (e.g., current) having a positive polarity.

Various additional electrical sources are shown in FIG. 7. For example, the configuration of FIG. 7 shows another positive electrical source 100G, along with negative electrical sources 100A-100E. As previously described in reference to FIG. 5, each of electrical sources 100A-100Z may be configured as either a positive or a negative electrical source, according to some embodiments.

Each negative electrical source 100A-100E is connected to a different one of electrode nodes 122A-122E. For example, negative electrical source 100A is connected to electrode node 122A; negative electrical source 100B is connected to electrode node 122B; negative electrical source 100C is connected to electrode node 122C; negative electrical source 100D is connected to electrode node 122D; and negative electrical source 100E is connected to electrode node 122E.

Switching unit 106A is connected to each of electrode nodes 122A-122D. Because positive electrical source 100F is connected to switching unit 106A, switching unit 106A may be configured to connect positive electrical source 100F to a selected one of electrode nodes 122A-122D.

Processor 58 (FIG. 3) may activate one or more of negative electrical sources 100A-100D at any given point in time. When negative electrical sources 100A-100D are activated, they are capable of delivering electrical stimulation of a negative polarity. Electrodes connected to electrode nodes that are connected these activated negative sources may then function as cathodes. For example, if processor 58 activates negative electrical source 100A, such that source 100A may deliver electrical stimulation of a negative polarity, the electrode connected to electrode node 122A (which is connected to negative electrical source 100A) functions as a cathode. Because each of electrode nodes 122A-122D are connected to a corresponding negative source, each of the electrodes connected to nodes 122A-122D may function as a cathode at any given point in time.

Processor 58 may also activate positive electrical source 100F. When positive electrical source 100F is activated, it is capable of delivering electrical stimulation of a positive polarity. Any electrode connected to an electrode node that is coupled to positive electrical source 100F upon its activation may function as an anode. Because switching unit 106A is connected to each of electrode nodes 122A-122D, switching unit 106A is capable of coupling positive electrical source 100F to any selected one of the electrodes connected to nodes 122A-122D. Thus, if switching unit 106A connects positive electrical source 100F to electrode node 122B, the electrode connected to 122B functions as an anode upon activation of positive electrical source 100F. Each of electrodes connected to nodes 122A-122D may therefore function as an anode at any given point in time.

In some embodiments, processor 58 may provide one or more signals to switching unit 106A to control switching unit 160A. For example, processor 58 may control switching unit 106A to connect positive electrical source 100F to a selected one of electrode nodes 122A-122D. Any a given point in time, any of the electrodes connected to nodes 122A-122D may function as either a cathode or anode, and may therefore be connected to either one of activated negative electrical sources 100A-100D or to activated positive electrical source 100F, according to one embodiment.

Although each electrode node 122A-122D is independently connected to a different negative electrical source, each electrode node 122A-122D may be operatively coupled (during activation of positive electrical source 100F) to one positive electrical source, according to the example configuration shown in FIG. 7. Thus, in this configuration, because each electrode node 122A-122D is not independently connected to a different positive electrical source, fewer overall components are utilized. The configuration of FIG. 7 includes only one positive electrical source 100F. As a result, this configuration may use a reduced physical area size, and take up less space, within stimulation generator 62. In addition, this configuration may consume less power from power source 66 (FIG. 3), which can have significant benefits in an implantable device.

In the example of FIG. 7, electrode node 122E is connected to negative electrical source 100E, but is not connected to switching unit 106A. Instead, electrode node 122E is directly connected to a positive electrical source 100G. Thus, in some cases, one or more electrode nodes, such as electrode node 122E, may be independently coupled to a positive electrical source. In one embodiment, these electrode nodes may be connected to housing electrodes that are located on a housing implantable stimulator 14 or IMD 40. In FIG. 7, the electrode connected to electrode node 122E may function as a cathode when negative electrical source 100E is activated, or may function as an anode when positive electrical source 100G is activated. In one embodiment, the electrodes connected to electrode nodes 122A-122D may be included within one or more leads, such as leads 16A-16B (FIG. 2) or 24A-24B (FIG. 2).

Figure 8:
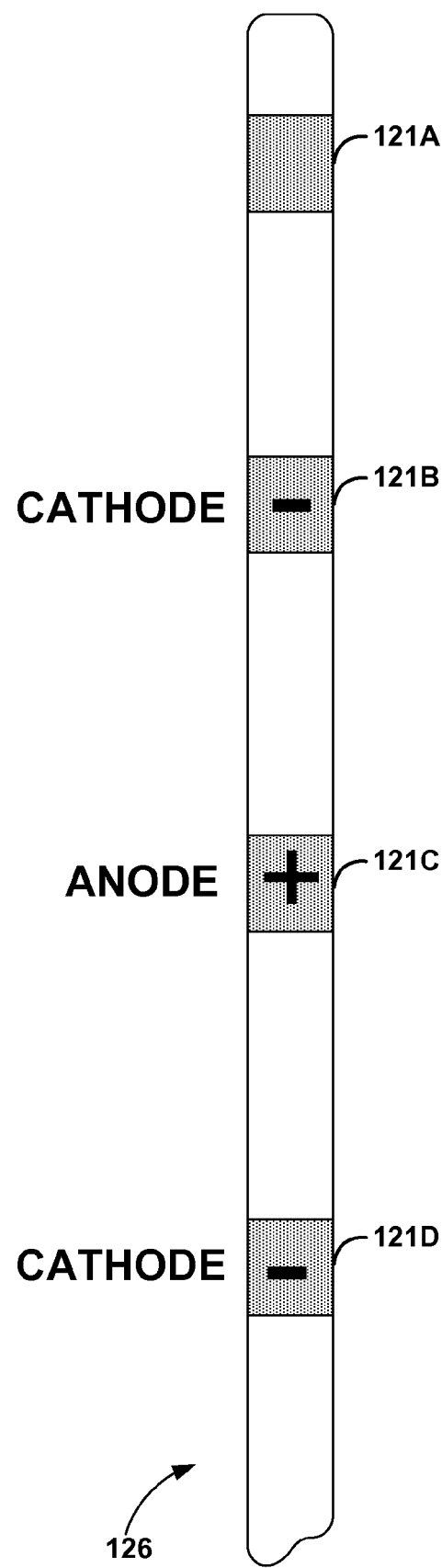
FIG. 8 is a conceptual diagram illustrating an example lead with electrodes configured as anodes and cathodes, according to one embodiment.

FIG. 8 is a conceptual diagram illustrating an example lead 126 that includes electrodes 121A-121D, according to one embodiment. In some cases, example lead 126 may comprise one of leads 16A-16B (FIG. 1) or leads 24A-24B (FIG. 2). Each of electrodes 121A-121D is connected to a corresponding electrode node 122A-122D shown in FIG. 7. Thus, electrode 121A is connected to electrode node 122A; electrode 121B is connected to electrode node 122B; electrode 121C is connected to electrode node 122C; and electrode 121D is connected to electrode node 122D.

In the example of FIG. 8, electrode 121B functions as a cathode, electrode 121C functions as an anode, and electrode 121D functions as a cathode. Thus, it is assumed that electrode node 122B (which is connected to electrode 121B) is connected to negative electrical source 100B, which has been activated by processor 58 (FIG. 3), that electrode node 122C is connected to an activated positive electrical source 100F via switching unit 106A, and that electrode node 122D is connected to an activated negative electrical source 100D. Because electrode 121A is not shown as either a cathode or an anode, it is assumed that negative electrical source 100A is not activated. Switching unit 106A is configured to selectively connect positive electrical source 100F to electrode node 122C upon receipt of one or more signals from processor 58 (FIG. 3), according to one embodiment.

Figure 9:
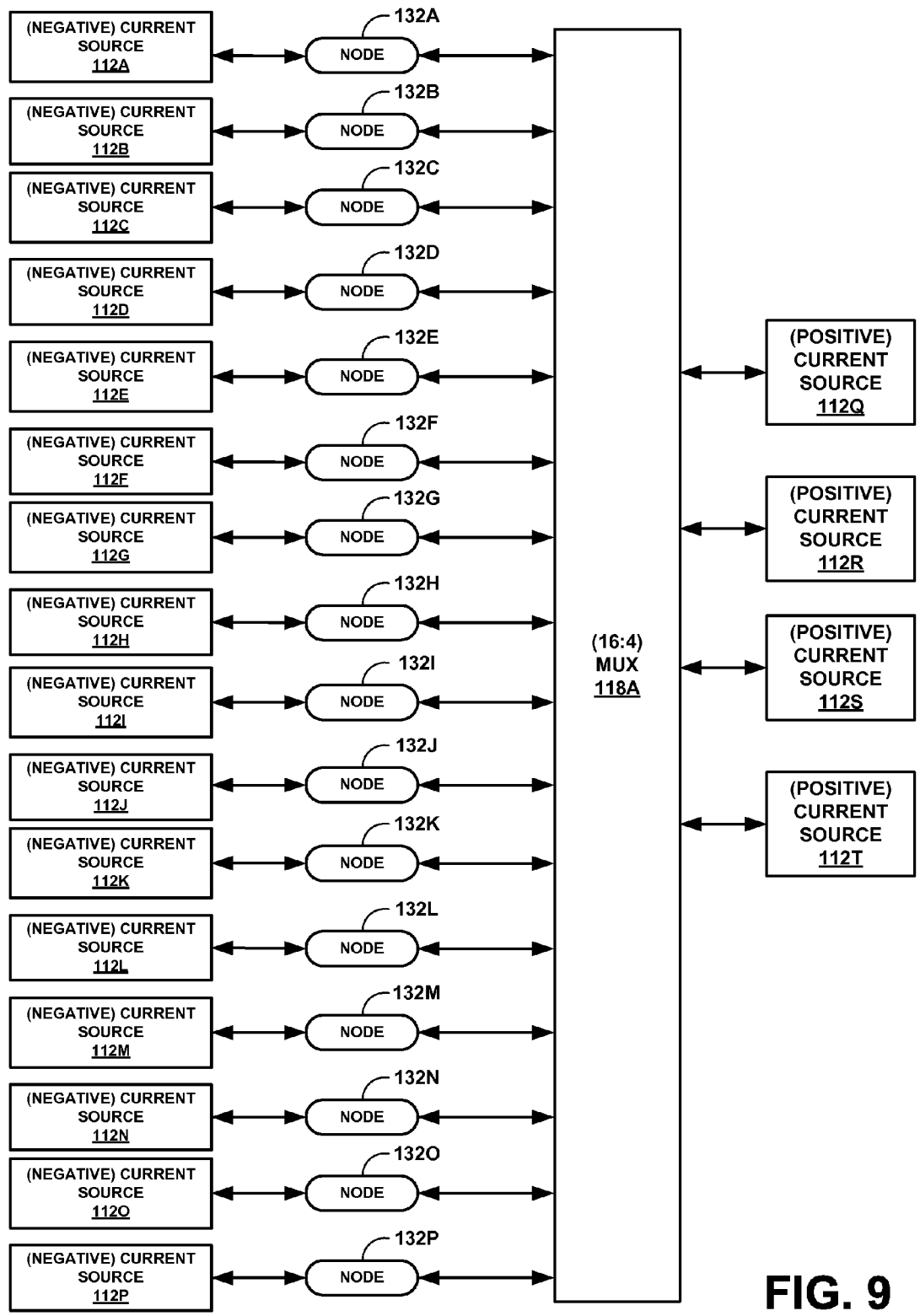
FIG. 9 is a block diagram illustrating an example configuration in which a multiplexer (MUX) of the pulse generator shown in FIG. 6 may connect multiple positive current sources to a selected one or more of a plurality of electrode nodes, and in which negative electrical sources are directly connected to respective electrode nodes, according to one embodiment.

FIG. 9 is a block diagram illustrating an example configuration in which a multiplexer (MUX) 118A of pulse generator 110 shown in FIG. 6 may connect multiple positive current sources 112Q-112T to a selected one or more of electrode nodes 132A-132P, according to one embodiment. In this embodiment, MUX 118A may be part of multiplexers 118 shown in FIG. 6. Current sources 112A-112Z comprise a set of negative current sources 112A-112P and a set of positive current sources 112Q-112T. Of course, the configuration shown in FIG. 9 is merely exemplary. Pulse generator 110 could include any number of positive and negative current sources, along with any number of multiplexers.

The example configuration of FIG. 9 includes a set of sixteen electrode nodes 132A-132P. These sixteen electrode nodes 132A-132P may be connected to sixteen corresponding electrodes included on one or more leads, such as leads 16A-16B (FIG. 1) or leads 24A-24B (FIG. 2). Each electrode node 132A-132P is connected to a different, respective negative current source 112A-112P. Each electrode node 132A-132P is also connected to MUX 118A.

MUX 118A is further connected to each of the four positive current sources 112Q-112T. Thus, in FIG. 9, MUX 118A comprises a 16:4 MUX. In this example, one MUX unit (118A) is capable of coupling multiple positive current sources 112Q-112T to a selected group of one or more of electrode nodes 132A-132P. MUX 118A may be configured to connect each of positive current sources 112Q-112T to a selected one of electrode nodes 132A-132P upon activation of the respective current source. In some cases, MUX 118A may contain switching elements that allow MUX 118A to selectively connect positive current source 112Q to a select one of a first group of four electrode nodes 132A-132D, to selectively connect positive current source 112R to a select one of a second group of four electrode nodes 132E-132H, to selectively connect positive current source 112S to a select one of a third group of four electrode nodes 132I-132L, and to selectively connect positive current source 112T to a select one of a fourth group of four electrode nodes 132M-132P.

In the configuration shown in FIG. 9, each electrode node 132A-132P may be connected to an electrode that functions as a cathode when coupled to a respective, activated negative current source 112A-112P. When coupled, via MUX 118A, to one of positive current sources 112Q-112T, select ones of electrode nodes 132A-132P may be connected to electrodes that function as anodes.

Figure 10:
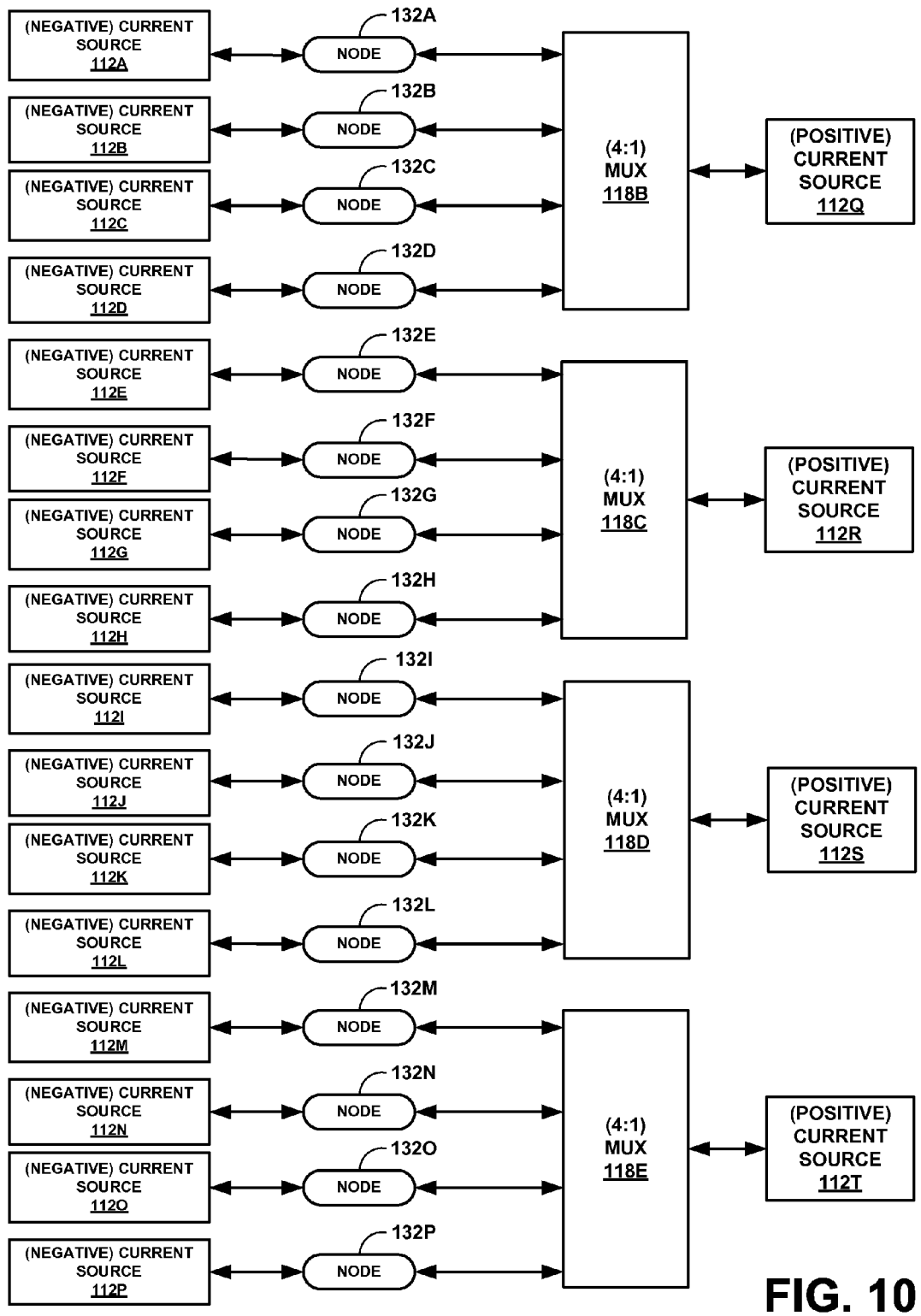
FIG. 10 is a block diagram illustrating an example configuration in which multiple MUXs of the pulse generator shown in FIG. 6 may connect each of multiple positive current sources to a selected one of a plurality of electrode nodes, and in which negative electrical sources are directly connected to respective electrode nodes, according to another embodiment.

FIG. 10 is a block diagram illustrating an example configuration in which multiple multiplexers (MUXs) 118B-118E of pulse generator 110 shown in FIG. 6 may connect each of multiple positive current sources 112Q-112T to a selected one of electrode nodes 132A-132P, according to another embodiment. The primary difference between the configuration shown in FIG. 10 in comparison to the one shown in FIG. 9 is the use of multiple, separate MUXs 118B-118E. These MUXs 118B-118E may be part of multiplexers 118 shown in FIG. 6.

MUX 118B is connected to each of the four electrode nodes 132A-132D, and is also connected to positive current source 112Q. MUX 118C is connected to each of the four electrode nodes 132E-132H, and is also connected to positive current source 112R. MUX 118D is connected to each of the four electrode nodes 132I-132L, and is also connected to positive current source 112S. MUX 118E is connected to each of the four electrode nodes 132M-132P, and is also connected to positive current source 112T. As a result, each of MUXs 118B-118E comprises a 4:1 MUX.

In one embodiment, processor 58 (FIG. 3) may control MUX 118B to selectively connect positive current source 112Q, upon its activation, to one of electrode nodes 132A-132D, which is respectively coupled to an electrode that may function as an anode. Processor 58 may also control MUX 118C to selectively connect positive current source 112R, upon its activation, to one of electrode nodes 132E-132H. Processor 58 may control MUX 118D to selectively connect positive current source 112S, upon activation, to one of electrode nodes 132I-132L. And, processor 58 may further control MUX 118E to selectively connect positive current source 112T, upon its activation, to one of electrode nodes 132M-132P. Thus, during activation of one or more of positive current sources 112Q-112T, anywhere from one to four electrodes respectively coupled to electrode nodes 132A-132P may function as anodes, according to one embodiment.

Figure 11:
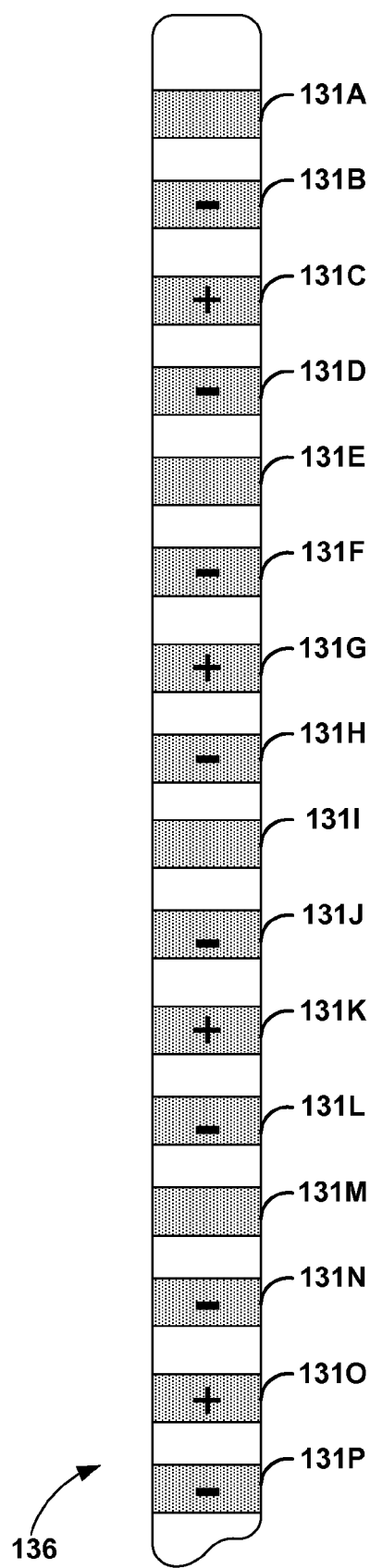
FIG. 11 is a conceptual diagram illustrating an example lead that includes sixteen electrodes corresponding to the sixteen electrode nodes shown in FIG. 10, according to one embodiment.

FIG. 11 is a conceptual diagram illustrating an example lead 136 that includes sixteen electrodes 131A-131P, according to one embodiment. Of course, in other embodiments, these sixteen electrodes could be included on a plurality of different leads.

In the example of FIG. 11, it is assumed that electrodes 131A-131P are each connected to a respective electrode node 132A-132P (shown in FIGS. 9 and 10). As shown in FIG. 11, electrodes 131B, 131D, 131F, 131H, 131J, 131L, 131N, and 131P function as cathodes, and that each of the four electrode nodes 131C, 131G, 131K, and 131O function as anodes. Therefore, it is assumed that respective electrode nodes 132B, 132D, 132F, 132H, 132J, 132L, 132N, and 132P are connected to corresponding activated negative current sources 112B, 112D, 112F, 112H, 112J, 112L, 112N, and 112P.

With respect to the anodes, MUX 118B is configured to connect electrode node 132C, which is connected to electrode 131C, to activated positive current source 112Q in the example of FIG. 11. Additionally, in this example, it is assumed that MUX 118C is configured to connect electrode node 132G to activated positive current source 112R, MUX 118D is configured to connect electrode node 132K to activated positive current source 112S, and MUX 118E is configured to connect electrode node 132O to activated positive current source 112T. As a result, respective electrodes 131C, 131G, 131K, and 131O in FIG. 11 may function as anodes.

Figure 12:
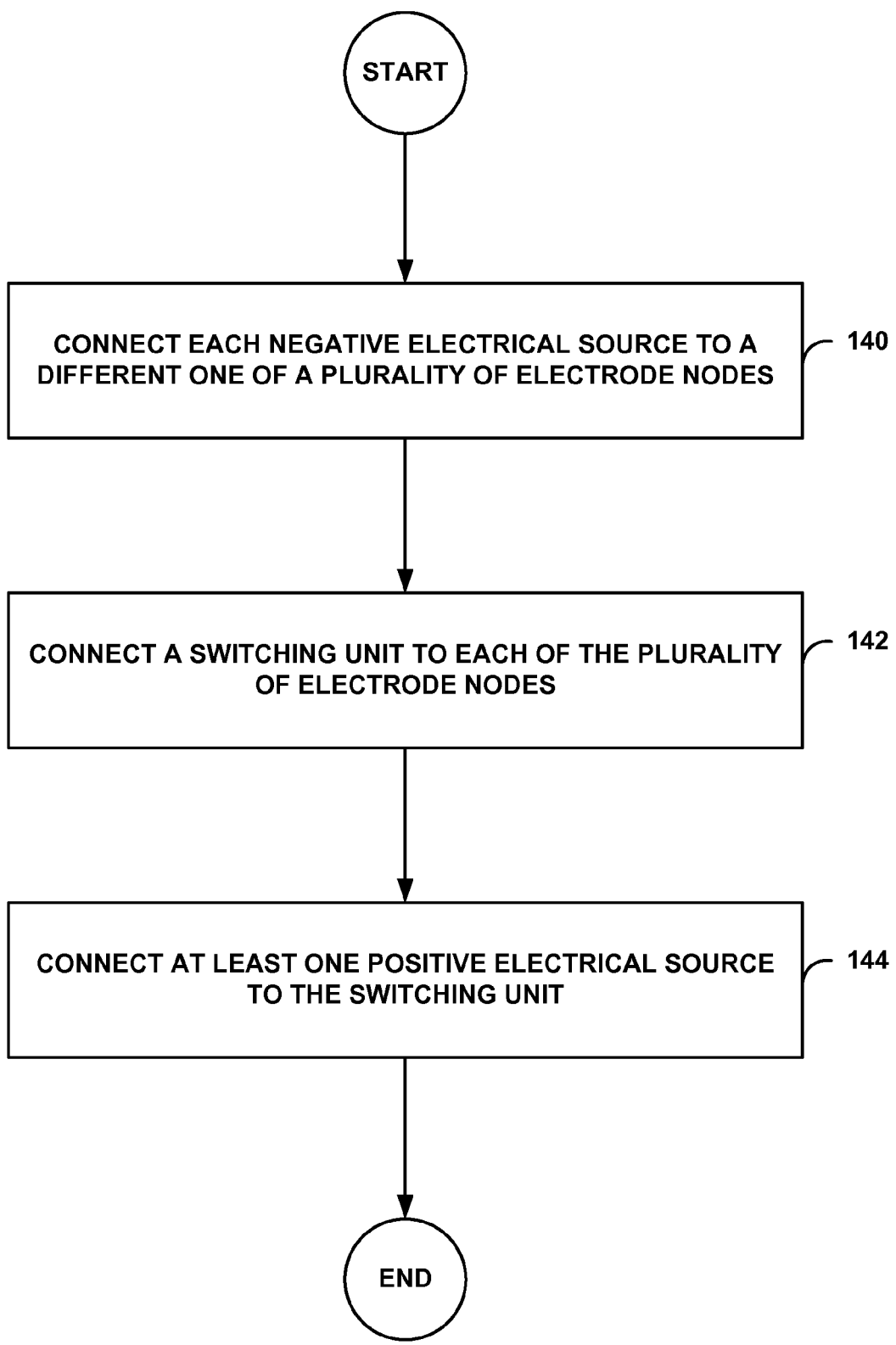
FIG. 12 is a flow diagram illustrating a method that may be performed to create and/or initialize the configurations that are shown in FIGS. 7, 9, and/or 10, according to one embodiment.

FIG. 12 is a flow diagram illustrating a method that may be performed to create and/or initialize the configurations that are shown in FIGS. 7, 9, and/or 10, according to one embodiment. Initially, each of a plurality of negative electrical sources in a stimulation generator, such as negative electrical sources 100A-100D shown in FIG. 7, is directly connected to a different one of a plurality of electrode nodes, such as electrode nodes 122A-122D, respectively, shown in FIG. 7 (140). A switching unit in the stimulation generator, such as switching unit 106A, is also connected to each of the plurality of electrode nodes (142). In addition, at least one positive electrical source in the stimulation generator, such as the positive electrical source 100F shown in FIG. 7, is connected to the switching unit (144).

Upon activation of the at least one positive electrical source, the switching unit, which may comprise a multiplexer, is configured to connect the at least one positive electrical source to a selected one or more of the plurality of electrode nodes via the switching unit. For example, with reference to the example of FIG. 7, upon activation of positive electrical source 100F, switching unit 106A is configured to connect positive electrical source 100F to a selected one of the electrode nodes 122A-122D via switching unit 106A. With reference to the example of FIG. 9, upon activation of one or more of positive current sources 112Q-112T, MUX 118A, which may be part of a switching unit, is configured to connect positive current sources 112Q-112T to a selected one or more of the electrode nodes 132A-132P via MUX 118A. Any one or more of positive current sources 112Q-112T may be activated, and each activated positive current source may be connected to a selected one electrode node via the respective MUX to which it is connected.

In one embodiment, such as in the one shown in FIG. 10, a first plurality of negative current sources in the stimulation generator are each directly connected to a different one of a first plurality of electrode nodes, and a second plurality of negative electrical sources in the stimulation generator are each directly connected to a different one of a second plurality of electrode nodes. For example, as shown in FIG. 10, negative current sources 112A-112D are each directly connected to a different, respective one of electrode nodes 132A-132D, and negative current sources 112E-112H are each directly connected to a different, respective one of electrode nodes 132E-132H.

A first switching unit in the stimulation generator, such as MUX 118B, is connected to each of the first plurality of electrode nodes 132A-132D, and a second switching unit in the stimulation generator, such as MUX 118C, is connected each of the second plurality of electrode nodes 132E-132H. At least one positive electrical source in the simulation generator, such as positive current source 112Q, is connected to the first switching unit (MUX 118B), while at least one additional positive electrical source in the stimulation generator, such as positive current source 112R, is connected to the second switching unit (MUX 118C).

In one embodiment, the stimulation generator may comprise a pulse generator, such as pulse generator 110 shown in FIG. 6. In one embodiment, the plurality of negative electrical sources and the at least one positive electrical source are each selected from a group consisting of a current source and a voltage source. In the example of FIG. 6, each electrical source comprises a current source 112A-112Z.

Figure 13:
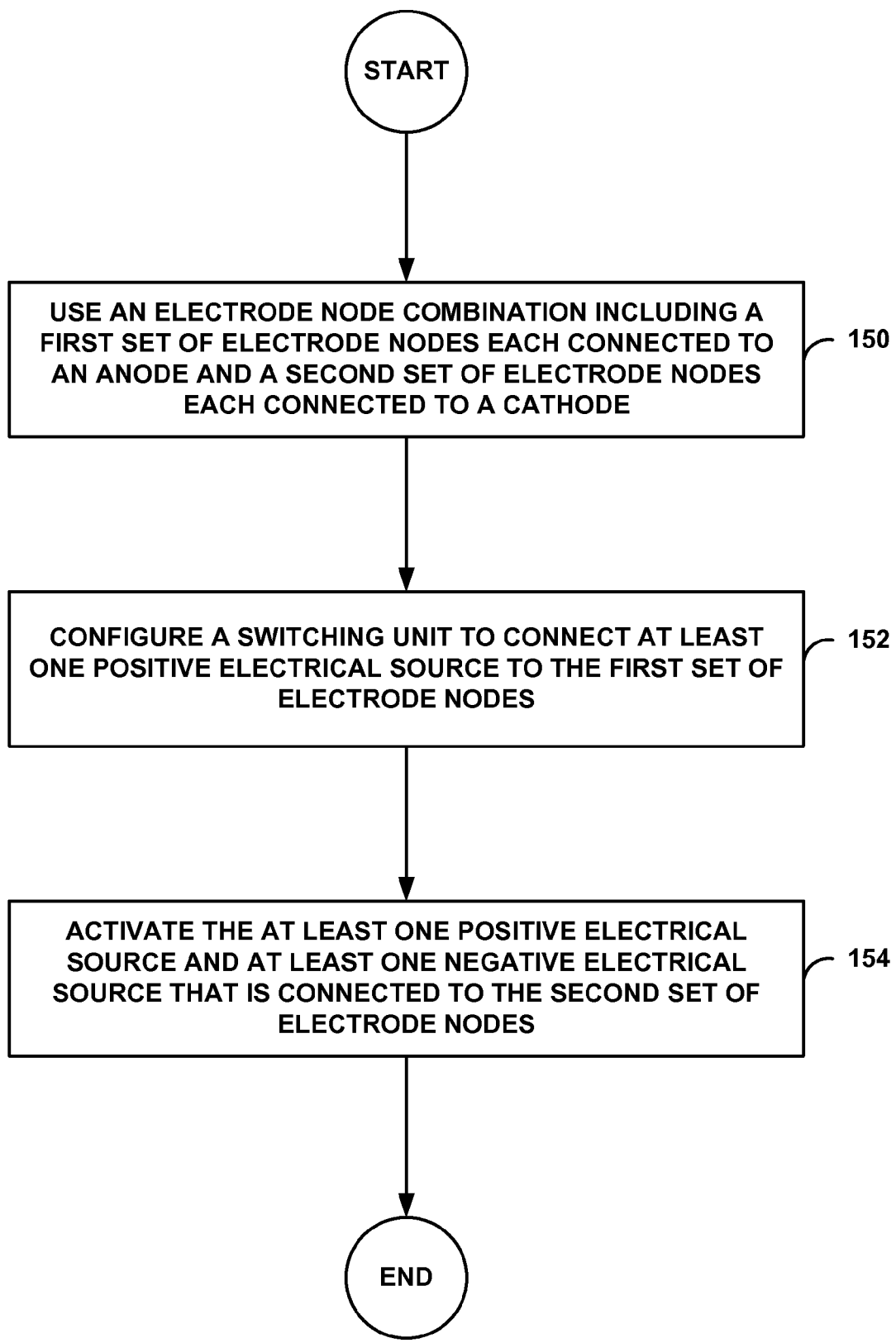
FIG. 13 is a flow diagram illustrating a method that may be performed by the stimulation generator shown in FIG. 5 and/or the pulse generator shown in FIG. 6 to connect at least one positive electrical source to a selected set of one or more electrode nodes, according to one embodiment.

FIG. 13 is a flow diagram illustrating a method that may be performed by stimulation generator 62 shown in FIG. 5 and/or pulse generator 110 shown in FIG. 6 to connect at least one positive electrical source to a selected set of one or more electrode nodes, according to one embodiment. For purposes of illustration only, it will be assumed that the method of FIG. 13 is performed by stimulation generator 62.

Stimulation generator 62 may use an electrode node combination for an implantable stimulator (150). The electrode node combination may be associated with a corresponding electrode combination. Each electrode node in the electrode node combination may be connected to a respective electrode in the corresponding electrode combination. Examples of electrode combinations are shown in FIGS. 8 and 11.

The identified electrode node combination includes a first set of one or more electrode nodes that are each connected to an anode, and a second set of one or more electrode nodes that are each connected to a cathode. Each anode comprises at least one electrode having a positive polarity, and each cathode comprises at least one electrode having a negative polarity.

Stimulation generator 62 configures a switching unit within switching units 106 to connect at least one positive electrical source in stimulation generator 62 to the first set of one or more electrode nodes that are each connected to an anode (152). The switching unit may comprise one or more multiplexers. The at least one positive electrical source may comprise at least one of electrical sources 100A-100Z that functions as a positive electrical source when activated.

Stimulation generator 62 activates the at least one positive electrical source. Stimulation generator 62 also activates at least one negative electrical source, wherein the at least one negative electrical source is directly connected to the second set of one or more electrode nodes that are each connected to a cathode (154). The at least one negative electrical source may comprise at least one of electrical sources 100A-100Z that functions as a negative electrical source when activated. The at least one negative electrical source and the at least one positive electrical source may each selected from a group consisting of a current source and a voltage source, according to one embodiment. In one embodiment, stimulation generator 62 may deactivate at least one additional negative electrical source that is connected to the first set of one or more electrode nodes.

In some embodiments, the at least one positive electrical source comprises a plurality of positive electrical sources, and the first set of one or more electrode nodes comprises a first plurality of electrode nodes each connected to an anode. In these embodiments, stimulation generator 62 may configure the switching unit within switching units 106 to connect each of the plurality of positive electrical sources to a selected one of the first plurality of electrode nodes, such as is shown in the example of FIG. 9, where the positive electrical sources comprise positive current sources.

In some embodiments, stimulation generator 62 identifies a second electrode node combination that includes a third set of one or more electrode nodes that are each connected to an anode and a fourth set of one or more electrode nodes that are each connected to a cathode. Stimulation generator 62 may configure a second switching unit within switching units 62 to connect at least one additional positive electrical source within sources 100A-100Z to third set of one or more electrode nodes. FIG. 10 shows an example having multiple switching units 118B-118E, which comprise multiplexers in this example. In one scenario, a first electrode node combination may include electrode nodes 132A-132D shown in FIG. 10 as connected to MUX 118B, and a second electrode node combination may include electrode nodes 132E-132H as connected to MUX 118C. Stimulation generator 62 may activate the at least one additional positive electrical source, and may also activate at least one additional negative electrical source within sources 100A-100Z, where the at least one additional negative electrical source is directly connected to the fourth set of one or more electrode nodes that are each connected to a cathode.

The techniques described in this disclosure may be implemented, at least in part, in hardware, software, firmware or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. The term "processor" or "processing circuitry" may generally refer to any of the foregoing logic circuitry, alone or in combination with other logic circuitry, or any other equivalent circuitry.

When implemented in software, the functionality ascribed to the systems and devices described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic media, optical media, or the like. The instructions may be executed to support one or more aspects of the functionality described in this disclosure.

Many embodiments of the invention have been described. Various modifications may be made without departing from the scope of the claims. These and other embodiments are within the scope of the following claims.

The invention claimed is:

1. An implantable stimulator, comprising:
a plurality of electrode nodes;
a processor; and
a stimulation generator coupled to the processor and to the electrode nodes, the stimulation generator comprising:
 a plurality of negative electrical sources that are each directly connected to a different one of the plurality of electrode nodes;
 a switching unit that is connected to each of the plurality of electrode nodes; and
 at least one positive electrical source connected to the switching unit,
wherein the switching unit is configured to connect the at least one positive electrical source to a selected one or more of the plurality of electrode nodes, and
wherein the plurality of electrode nodes are not configured to be connected to the at least one positive electrical source or any other positive electrical source in the stimulation generator except through the switching unit.

2. The implantable stimulator of claim 1, wherein the processor controls the switching unit to connect the at least one positive electrical source to the selected one or more of the plurality of electrode nodes.

3. The implantable stimulator of claim 1, wherein one of the plurality of negative electrical sources is directly connected to a first electrode node in the plurality of electrode nodes, and wherein the switching unit is configured to connect the at least one positive electrical source to a second electrode node in the plurality of electrode nodes, such that a first electrode connected to the first electrode node comprises a cathode and a second electrode connected to the second electrode node comprises an anode.

4. The implantable stimulator of claim 1, wherein the at least one positive electrical source comprises a plurality of positive electrical sources that are each connected to the switching unit, and wherein the switching unit is configured to connect each of the plurality of positive electrical sources to a selected one of the plurality of electrode nodes.

5. The implantable stimulator of claim 1, wherein the stimulation generator further comprises:
a second plurality of negative electrical sources that are each directly connected to a different one of a second plurality of electrode nodes;
a second switching unit that is connected to the second plurality of electrode nodes; and
at least one additional positive electrical source connected to the second switching unit,
wherein the second switching unit is configured to connect the at least one additional positive electrical source to a selected one or more of the second plurality of electrode nodes, and
wherein the second plurality of electrode nodes are not configured to be connected to the at least one additional positive electrical source or any other positive electrical source in the stimulation generator except through the second switching unit.

6. The implantable stimulator of claim 1, further comprising at least one lead that includes a plurality of electrodes, each of the electrodes connected to a respective one of the plurality of electrode nodes.

7. The implantable stimulator of claim 1, wherein the switching unit comprises at least one multiplexer.

8. The implantable stimulator of claim 1, wherein the stimulation generator comprises a pulse generator, and wherein the plurality of negative electrical sources and the at least one positive electrical source are each selected from a group consisting of a current source and a voltage source.

9. The implantable stimulator of claim 1, wherein neither the plurality of electrode nodes nor any other electrode nodes in the implantable stimulator are configured to be connected to any positive electrical source in the stimulation generator except through the switching unit.

10. A stimulation generator, comprising:
a plurality of negative electrical sources that are each directly connected to a different one of a plurality of electrode nodes that are coupled to the stimulation generator;
a switching unit that is connected to each of the plurality of electrode nodes; and
at least one positive electrical source connected to the switching unit,
wherein the switching unit is configured to connect the at least one positive electrical source to a selected one or more of the plurality of electrode nodes, and
wherein the plurality of electrode nodes are not configured to be connected to the at least one positive electrical source or any other positive electrical source in the stimulation generator except through the switching unit.

11. The stimulation generator of claim 10, wherein one of the plurality of negative electrical sources is directly connected to a first electrode node in the plurality of electrode nodes, and wherein the switching unit is configured to connect the at least one positive electrical source to a second electrode node in the plurality of electrode nodes, such that a first electrode connected to the first electrode node comprises a cathode and a second electrode connected to the second electrode node comprises an anode.

12. The stimulation generator of claim 10, wherein the at least one positive electrical source comprises a plurality of positive electrical sources that are each connected to the switching unit, and wherein the switching unit is configured to connect each of the plurality of positive electrical sources to a selected one of the plurality of electrode nodes.

13. The stimulation generator of claim 10, wherein the stimulation generator further comprises:
a second plurality of negative electrical sources that are each directly connected to a different one of a second plurality of electrode nodes;
a second switching unit that is connected to the second plurality of electrode nodes; and
at least one additional positive electrical source connected to the second switching unit, wherein the second switching unit is configured to connect the at least one additional positive electrical source to a selected one or more of the second plurality of electrode nodes, and wherein the second plurality of electrode nodes are not configured to be connected to the at least one additional positive electrical source any other positive electrical source in the stimulation generator except through the second switching unit.

14. The stimulation generator of claim 10, wherein the switching unit comprises at least one multiplexer.

15. The stimulation generator of claim 10, wherein the stimulation generator comprises a pulse generator, and wherein the plurality of negative electrical sources and the at least one positive electrical source are each selected from a group consisting of a current source and a voltage source.

16. The stimulation generator of claim 10, wherein neither the plurality of electrode nodes nor any other electrode nodes coupled to the stimulation generator are configured to be connected to any positive electrical source in the stimulation generator except through the switching unit.

17. A method comprising:
directly connecting each of a plurality of negative electrical sources in a stimulation generator to a different one of a plurality of electrode nodes;
connecting a switching unit in the stimulation generator to each of the plurality of electrode nodes; and
connecting at least one positive electrical source in the stimulation generator to the switching unit,
wherein the switching unit is configured to connect the at least one positive electrical source to a selected one or more of the plurality of electrode nodes, and
wherein the plurality of electrode nodes are not configured to be connected to the at least one positive electrical source or any other positive electrical source in the stimulation generator except through the switching unit.

18. The method of claim 17, further comprising:
directly connecting each of a second plurality of negative electrical sources in the stimulation generator to a different one of a second plurality of electrode nodes;
connecting a second switching unit in the stimulation generator to each of the second plurality of electrode nodes; and
connecting at least one additional positive electrical source in the stimulation generator to the second switching unit,
wherein the second switching unit is configured to connect the at least one additional positive electrical source to a selected one or more of the second plurality of electrode nodes, and
wherein the second plurality of electrode nodes are not configured to be connected to the at least one additional positive electrical source or any other positive electrical source in the stimulation generator except through the second switching unit.

19. The method of claim 17, wherein the switching unit comprises at least one multiplexer.

20. The method of claim 17, wherein the stimulation generator comprises a pulse generator, and wherein the plurality of negative electrical sources and the at least one positive electrical source are each selected from a group consisting of a current source and a voltage source.

21. The method of claim 17, wherein neither the plurality of electrode nodes nor any other electrode nodes coupled to the stimulation generator are configured to be connected to any positive electrical source in the stimulation generator except through the switching unit.

22. A method comprising:
using an electrode node combination for an implantable stimulator that includes a first set of one or more electrode nodes that are each connected to an anode, wherein the electrode node combination further includes a second set of one or more electrode nodes that are each connected to a cathode;
configuring a switching unit in a stimulation generator to connect at least one positive electrical source in the stimulation generator to the first set of one or more electrode nodes, wherein the first set of one or more electrode nodes is not configured to be connected to the at least one positive electrical source or any other positive electrical source in the stimulation generator except through the switching unit;
activating the at least one positive electrical source; and
activating at least one negative electrical source in the stimulation generator, wherein the at least one negative electrical source is directly connected to the second set of one or more electrode nodes.

23. The method of claim 22, further comprising:
deactivating at least one additional negative electrical source that is connected to the first set of one or more electrode nodes.

24. The method of claim 22, wherein the at least one positive electrical source comprises a plurality of positive electrical sources, wherein the first set of one or more electrode nodes comprises a first plurality of electrode nodes, and wherein the method comprises configuring the switching unit to connect each of the plurality of positive electrical sources to a selected one of the first plurality of electrode nodes.

25. The method of claim 22, further comprising:
using a second electrode node combination for the implantable stimulator that includes a third set of one or more electrode nodes that are each connected to an anode, wherein the second electrode node combination further includes a fourth set of one or more electrode nodes that are each connected to a cathode;
configuring a second switching unit in the stimulation generator to connect at least one additional positive electrical source in the stimulation generator to the third set of one or more electrode nodes, wherein the third set of one or more electrode nodes is not configured to be connected to the at least one additional positive electrical source or any other positive electrical source in the stimulation generator except through the second switching unit;
activating the at least one additional positive electrical source; and
activating at least one additional negative electrical source in the stimulation generator, wherein the at least one additional negative electrical source is directly connected to the fourth set of one or more electrode nodes.

26. The method of claim 22, wherein the switching unit comprises at least one multiplexer.

27. The method of claim 22, wherein the stimulation generator comprises a pulse generator, and wherein the at least one negative electrical source and the at least one positive electrical source are each selected from a group consisting of a current source and a voltage source.

28. The method of claim 22, wherein neither the first set of one or more electrode nodes nor any other electrode nodes in the implantable stimulator are configured to be connected to any positive electrical source in the stimulation generator except through the switching unit.

29. An apparatus comprising:
means for using an electrode node combination for an implantable stimulator that includes a first set of one or more electrode nodes that are each connected to an anode, wherein the electrode node combination further includes a second set of one or more electrode nodes that are each connected to a cathode;

means for configuring a switching unit in a stimulation generator to connect at least one positive electrical source in the stimulation generator to the first set of one or more electrode nodes, wherein the first set of one or more electrode nodes is not configured to be connected to the at least one positive electrical source or any other positive electrical source in the stimulation generator except through the switching unit;

means for activating the at least one positive electrical source; and means for activating at least one negative electrical source in the stimulation generator, wherein the at least one negative electrical source is directly connected to the second set of one or more electrode nodes.

\* \* \* \* \*